US010942185B2

(12) United States Patent
Chao et al.

(10) Patent No.: US 10,942,185 B2
(45) Date of Patent: Mar. 9, 2021

(54) THERAPEUTIC AND DIAGNOSTIC METHODS FOR MANIPULATING PHAGOCYTOSIS THROUGH CALRETICULIN AND LOW DENSITY LIPOPROTEIN-RELATED RECEPTOR

(71) Applicant: The Board of Trustees of the Leland Stanford Junior University, Stanford, CA (US)

(72) Inventors: Mark P. Chao, Mountain View, CA (US); Rachel Weissman-Tsukamoto, Stanford, CA (US); Siddhartha Jaiswal, San Francisco, CA (US); Ravindra Majeti, Palo Alto, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/172,666

(22) Filed: Jun. 3, 2016

(65) Prior Publication Data

US 2016/0289326 A1 Oct. 6, 2016

Related U.S. Application Data

(62) Division of application No. 13/996,390, filed as application No. PCT/US2011/066580 on Dec. 21, 2011, now abandoned.

(60) Provisional application No. 61/459,909, filed on Dec. 21, 2010.

(51) Int. Cl.
| | |
|---|---|
| *C07K 14/435* | (2006.01) |
| *G01N 33/574* | (2006.01) |
| *C07K 16/28* | (2006.01) |
| *A61K 35/28* | (2015.01) |
| *A61K 39/395* | (2006.01) |
| *C12Q 1/6886* | (2018.01) |
| *G01N 33/68* | (2006.01) |
| *G01N 33/569* | (2006.01) |
| *A61K 39/00* | (2006.01) |

(52) U.S. Cl.
CPC ....... *G01N 33/57496* (2013.01); *A61K 35/28* (2013.01); *A61K 39/3955* (2013.01); *C07K 14/435* (2013.01); *C07K 16/2896* (2013.01); *C12Q 1/6886* (2013.01); *G01N 33/56966* (2013.01); *G01N 33/57492* (2013.01); *G01N 33/6872* (2013.01); *A61K 2039/505* (2013.01); *C07K 16/2803* (2013.01); *C07K 2317/73* (2013.01); *C07K 2317/76* (2013.01); *G01N 2333/47* (2013.01); *G01N 2333/4722* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,518,397 | B1 | 2/2003 | Debhar |
| 8,263,344 | B2 | 9/2012 | Kroemer et al. |
| 8,951,527 | B2 | 2/2015 | Isenberg et al. |
| 2004/0236071 | A1 | 11/2004 | Holoshitz et al. |
| 2009/0004178 | A1 | 1/2009 | Obeid |
| 2009/0005302 | A1 | 1/2009 | Obeid |
| 2009/0010952 | A1 | 1/2009 | Obeid |

OTHER PUBLICATIONS

Tame (J. Comput. Aided Mol. Des. Mar. 1999; 13 (2): 99-108).*
Dixon (Proteins. 1997; Suppl 1: 198-204).*
Lensink et al. (Proteins. 2007; 69: 704-718).*
Waterhouse et al (Apoptosis, 12:631-634, 2007).*
Chao et al., "Anti-CD47 Antibody Synergizes with Rituximab to Promote Phagocytosis and eradicate Non-Hodgkin Lymphoma", Cell, Sep. 3, 2010, pp. 699-713, 142(5), Elsevier, Inc., Amsterdam, Netherlands.
Gardai et al., "Cell-Surface Calreticulin Initiates Clearance of Viable or Apoptotic Cells through trans-Activation of LRP on the Phagocyte", Cell, Oct. 21, 2005, pp. 321-334, 123, Elsevier, Inc., Amsterdam, Netherlands.
Obeid et al., "Calreticulin exposure dictates the immunogenicity of cancer cell death", Nat Med, Jan. 2007, pp. 54-61, 13(1), Nature Publishing, London, United Kingdom.
Colombo et al., "Calreticulin exposure is required for the immunogenicity of gamma-irradiation and UVC light-induced apoptosis", Cell Death Differ, Jul. 27, 2007, pp. 1848-1850, 14(10).
Michalak et al., "Calreticulin, a multi-process calcium-buffering chaperone of the endoplasmic reticulum", Biochem J 2009, pp. 651-666, 417, Biochemical Society, London, United Kingdom.
Orr et al., "Low density lipoprotein receptor-related protein is a calreticulin coreceptor that signals focal adhesion disassembly", J Cell Biol, Nov. 6, 2003, pp. 179-189, vol. 161(6):1, The Rockefeller University Press, New York, NY.
Panaretakis et al., "The co-translocation of ERp57 and calreticulin determines the immunogenicity of cell death" Cell Death and Differentiation, Mar. 31, 2008, pp. 1499-1509, 15, Nature Publishing Group, London, United Kingdom.
Majeti et al., "CD47 Is an Adverse Prognostic Factor and Therapeutic Antibody Target on Human Acute Myeloid Leukemia Stem Cells", Cell, Jul. 23, 2009, pp. 286-299, 138(2), NIH Public Access, Bethesda, MD.
Liu et al., "Endoplasmic reticulum chaperones GRP78 and calreticulin prevent oxidative stress, Ca2+ disturbances, and cell death in renal epithelial cells", J Bioi Chem. Aug. 29, 1997, pp. 21751-21759, vol. 272, No. 35, The American Society for Biochemistry and Molecular Biology, Inc., Rockville, MD.
Wemeau et al., "Calreticulin exposure on malignant blasts predicts a cellular anticancer immune response in patients with acute myeloid leukemia", Cell Death Dis., Dec. 1, 2010, pp. 1-9, 1: e104, Macmillan Publishers Limited, London, United Kingdom.

(Continued)

*Primary Examiner* — Brad Duffy
(74) *Attorney, Agent, or Firm* — Pamela J. Sherwood; Bozicevic, Field & Francis LLP

(57) ABSTRACT

Therapeutic and diagnostic methods are provided, which methods relate to the expression of calreticulin on cancer cells and hematopoietic cells.

4 Claims, 14 Drawing Sheets

Specification includes a Sequence Listing.

(56) References Cited

OTHER PUBLICATIONS

Eriksson et al., "T-cell expression of CD91—a marker of unresponsiveness to anti-TNF therapy in rheumatoid arthritis", APMIS, Jul. 29, 2010, pp. 837-845, 118(11), Wiley Munksgaard, Hoboken, NJ.
Jaiswal et al., "CD47 Is Upregulated on Circulating Hematopoietic Stem Cells and Leukemia Cells to Avoid Phagocytosis", Cell, Jul. 24, 2009, pp. 271-285, 138, Elsevier, Inc., Amsterdam, Netherlands.
Obeid et al., "Ecto-calreticulin in immunogenic chemotherapy", Immunological Reviews, 2007, pp. 22-34, vol. 220, Blackwell Munksgaard, Oxford, United Kingdom.
Goicoechea et al., "Cell Surface Calreticulin: Role in Signaling Thrombospondin Anti-Adhesive Activity", Springer Science & Business Media, Dec. 6, 2012, pp. 193-204, Plenum Publishing, New York, NY.
Wang et al., "Platelet a2B1 integrin activation: contribution of ligand internalization and the a2-cytoplasmic domain", Blood, Aug. 15, 2003; pp. 1307-1315, vol. 102, No. 4, The American Society of Hematology, Washington, D.C.

\* cited by examiner

Post-sort

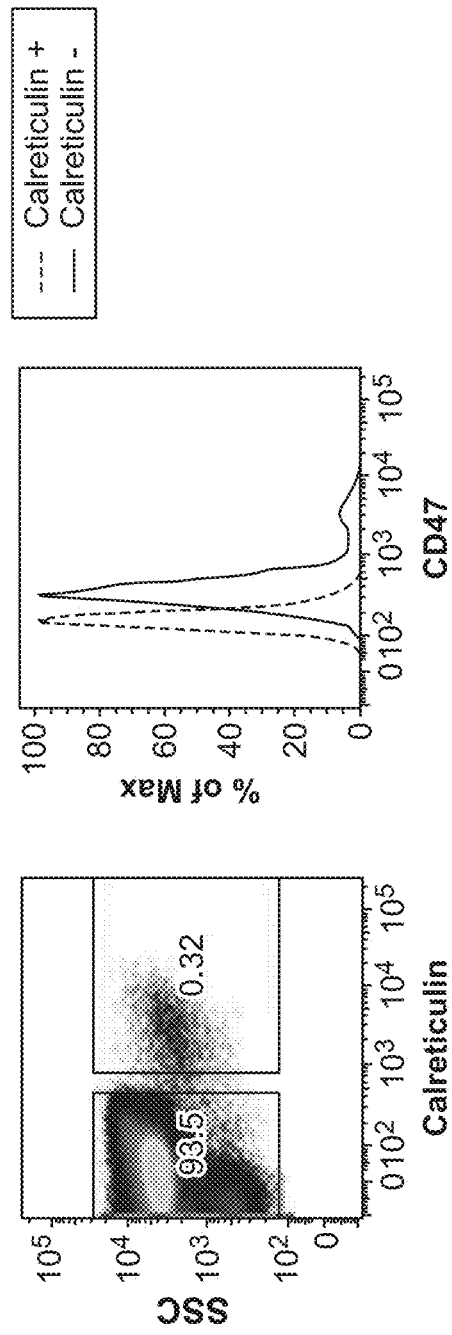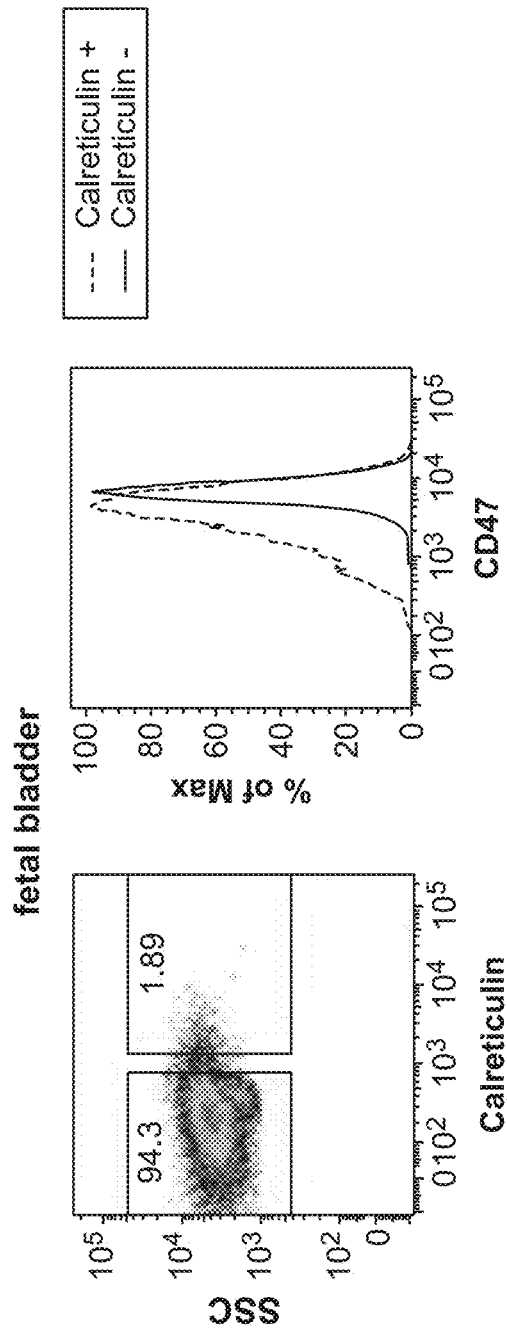
Figure 7A
Figure 7B

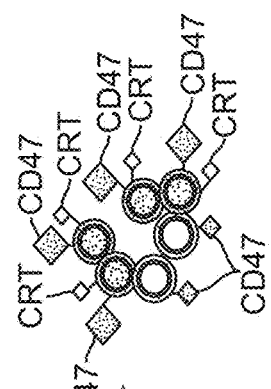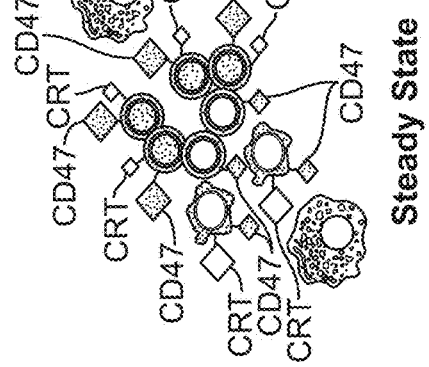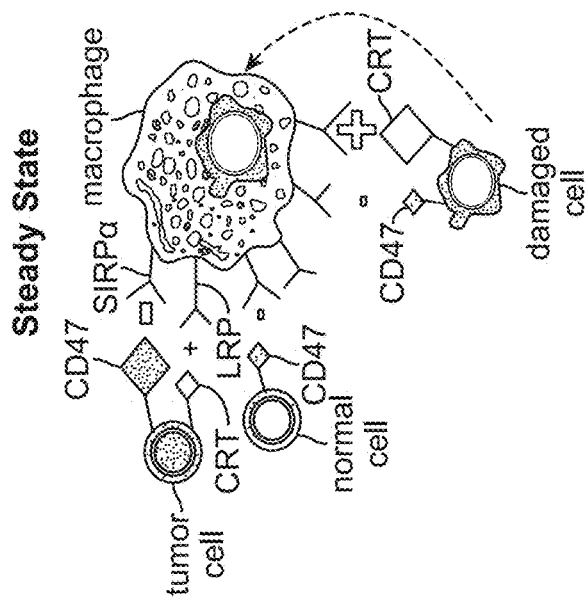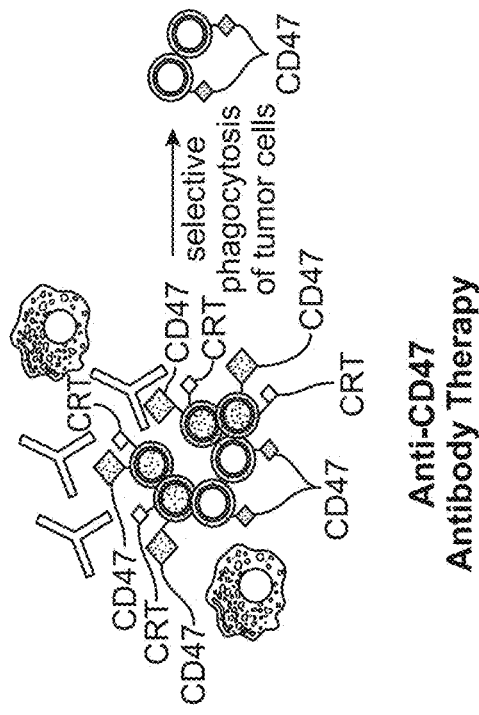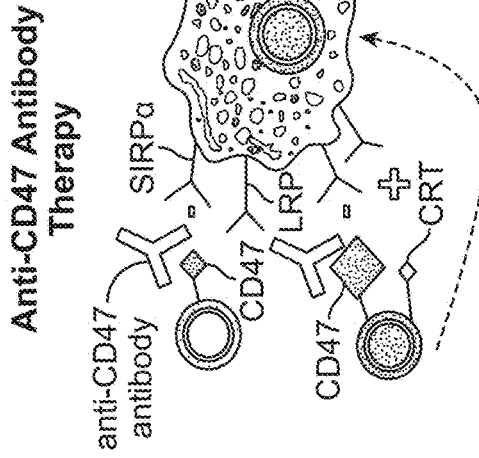
Figure 11A  Figure 11B  Figure 11C  Figure 11D Paca-2 (human pancreatic cell line)

Human primary neuroendocrine tumor (NET) sample with pancreas origin
EpCAM (red)
CRT (green)
NET LiverMet

THERAPEUTIC AND DIAGNOSTIC METHODS FOR MANIPULATING PHAGOCYTOSIS THROUGH CALRETICULIN AND LOW DENSITY LIPOPROTEIN-RELATED RECEPTOR

CROSS-REFERENCE

This application claims benefit and is a Divisional of application of Ser. No. 13/996,390 filed Jan. 24, 2014, which is a 371 application and claims the benefit of PCT Application No. PCT/US2011/066580, filed Dec. 21, 2011, which claims benefit of U.S. Provisional Patent Application No. 61/459,909, filed Dec. 21, 2010, which applications are incorporated herein by reference in their entirety.

GOVERNMENT RIGHTS

This invention was made with Government support under contracts HL058770 and CA139490 awarded by the National Institutes of Health. The Government has certain rights in the invention.

BACKGROUND

The reticuloendothelial system (RES) is a part of the immune system. The RES consists of the phagocytic cells located in reticular connective tissue, primarily monocytes and macrophages. The RES consists of 1) circulating monocytes; 2) resident macrophages in the liver, spleen, lymph nodes, thymus, submucosal tissues of the respiratory and alimentary tracts, bone marrow, and connective tissues; and 3) macrophage-like cells including dendritic cells in lymph nodes, Langerhans cells in skin, and microglial cells in the central nervous system. These cells accumulate in lymph nodes and the spleen. The RES functions to clear pathogens, particulate matter in circulation, and aged or damaged hematopoietic cells.

To eliminate foreign cells or particles in the innate immune response, macrophage-mediated phagocytosis is induced when the phosphatidylserine receptor (PSR) reacts to phosphatidylserine (PS), which can be externalized from the membranes of dead cells, such as apoptotic and necrotic cells. In turn, the interaction between PS and PSR plays a crucial role in the clearance of apoptotic cells by macrophages. Once phagocytosis has been performed by macrophages, the inflammatory response is downregulated by an increase in factors such as IL-10, TGF-$\beta$, and prostaglandin E2 (PGE2). The strict balance between the inflammatory and anti-inflammatory responses in both innate and adaptive immunity plays a critical role in maintaining cellular homeostasis and protecting a host from extrinsic invasion.

The causal relationship between inflammation and the neoplastic progression is a concept widely accepted. Data now support the concept of cancer immunosurveillance—that one of the physiologic functions of the immune system is to recognize and destroy transformed cells. However, some tumor cells are capable of evading recognition and destruction by the immune system. Once tumor cells have escaped, the immune system may participate in their growth, for example by promoting the vascularization of tumors.

Both adaptive and innate immune cells participate in the surveillance and the elimination of tumor cells, but monocytes/macrophages may be the first line of defense in tumors, as they colonize rapidly and secrete cytokines that attract and activate dendritic cells (DC) and natural killer (NK) cells, which in turn can initiate the adaptive immune response against transformed cells.

Malignant cellular transformation occurs through a progression of genetic mutations and epigenetic reprogramming that activate oncogenes and inactivate tumor suppressor pathways leading to inheritance of several hallmarks shared by most cancer cells including: self-sufficiency in growth signals, insensitivity to anti-growth signals, tissue invasion and metastasis, poorly regulated replicative potential, sustained angiogenesis, and evasion of cell death by a variety of pathways, including apoptosis. In addition to these cell intrinsic properties, recent evidence suggests that many cancers are also able to evade the immune system through several distinct mechanisms.

Recently it was shown that evasion of phagocytosis through upregulation of the anti-phagocytic signal CD47 is another mechanism by which tumor cells escape immunosurveillance. CD47 is a pentaspanin cell surface protein that serves as a signal inhibiting phagocytosis through ligation of its receptor SIRP$\alpha$ on phagocytic cells. Disruption of the CD47-SIRP$\alpha$ interaction can be therapeutically targeted with a monoclonal blocking antibody against CD47, which enables phagocytosis of acute myeloid leukemia (AML), bladder cancer, and non-Hodgkin lymphoma (NHL) cells in vitro and in vivo. In contrast, administration of anti-mouse CD47 antibody caused minimal toxicity, despite broad expression of CD47 on normal tissues.

CD47 has also been implicated in the regulation of phagocytosis of apoptotic cells, as these cells become phagocytosed due to loss of CD47 expression and coordinated upregulation of cell surface calreticulin. During apoptosis, cell surface calreticulin serves as a pro-phagocytic signal by binding to its macrophage receptor, low density lipoprotein-related protein (LRP), which leads to engulfment of the target cell.

Exploration of mechanisms by which cells avoid being cleared by phagocytosis can provide insight into ways for improving transplantation success of hematopoietic and progenitor stem cells, and improved methods of removing cancer cells from the body. The present invention satisfies these, and other, needs.

SUMMARY OF THE INVENTION

Therapeutic and diagnostic methods are provided, which methods relate to the expression of calreticulin.

In some embodiments of the invention, the expression of calreticulin (CTR) on cancer cells, including without limitation cancer cells prior to treatment with a chemotherapeutic drug, is utilized to enhance killing of the cancer cells. Cancer cells can be contacted with an agonist of CTR, e.g. an agonistic antibody, particularly one that activates LRP, in the presence of phagocytic cells in order to enhance phagocytosis of the cancer cells. In some such embodiments, the CTR agonist is administered in combination with an agent that blocks CD47 signaling, e.g. soluble SIRP$\alpha$, anti-CD47, and the like. Included in such agents are bi-specific antibodies targeted to both CD47 and CTR, or CD47 and LRP. Also included are agents comprising a CD47 blocking moiety and an active portion of CTR protein.

In related embodiments, cancer cells, including without limitation cancer cells prior to treatment with a chemotherapeutic drug, are contacted with an agent that selectively binds to CRT, including antibodies, soluble LRP, etc., which agent is optionally conjugated to a toxic moiety, e.g. a radionuclide, toxin, etc. to induce killing of the cell to which the agent has bound.

In other therapeutic methods, hematopoietic cells, including without limitation HSC, hematopoietic progenitors, normal bone marrow, or mobilized peripheral blood for patients with a clinical indication for hematopoietic transplantation, are protected from phagocytosis in circulation by providing a host animal with an agent that blocks the interaction between CRT and LRP, e.g. an antibody selective for CRT, an antibody selective for LRP, soluble CRT or LRP, a CRT blocking peptide, and the like, is administered, which blocks the pro-phagocytic signal and decreases the clearance of the hematopoietic cells from circulation. In some embodiments of the invention, the agent, e.g. peptide, soluble CRT, etc. is provided as a fusion protein, for example fused to an Fc fragment, e.g., IgG1 Fc, IgG2 Fc, Ig A Fc etc.

In another embodiment, methods are provided for targeting or depleting cancer stem cells, the method comprising contacting a population of cells, e.g. blood from a cancer patient, with a reagent that specifically binds CTR in order to target or deplete the cancer stem cells. In certain aspects, the reagent is an antibody conjugated to a cytotoxic agent, e.g. radioactive isotope, chemotherapeutic agent, toxin, etc. In some embodiments, the depletion is performed on an ex vivo population of cells, e.g. the purging of autologous stem cell products (mobilized peripheral blood or bone marrow) for use in autologous transplantation for cancer patients.

Detection of calreticulin expression, e.g. cell surface protein, mRNA, etc., particularly cell surface protein, is used alone or in conjunction with CD47 expression for clinical diagnostic applications including primary diagnosis of cancers, monitoring of interval disease progression, and monitoring of minimal residual disease status, including without limitation hematopoietic malignancies including acute myelogenous leukemia (AML), chronic myelogenous leukemia (CML), acute lymphocytic leukemia (ALL); and non-Hodgkin lymphoma (NHL). Cancer stem cells of interest also include carcinomas, e.g. squamous cell carcinoma, ovarian carcinoma, etc.; glioblastomas, and the like. Of interest is included the detection and treatment of cells prior to chemotherapeutic or radiation treatment. Detection of calreticulin on normal cells or tissues, especially hematopoietic stem and progenitor cells, in various states of malignancy, inflammation, and chemotherapy can guide the timing of anti-CD47 therapies for a variety of cancers; treatments would be held back during high frequency hematopoietic cell or normal tissue expression of calreticulin until calreticulin expression levels decreased to minimal levels.

In a related embodiment, an agent that selectively binds to CRT, e.g. soluble LRP, anti-CTR antibody, etc. is labeled with a detectable moiety, e.g. a fluorophore, imaging radioisotope, etc. for clinical diagnostic imaging applications including primary diagnosis of cancers, monitoring of interval disease progression, and monitoring of minimal residual disease status. Imaging may be performed in vivo or ex vivo.

Detection of CTR expression is also used in prognosis of cancer, where increased levels of CTR are shown to be associated with a worse clinical prognosis in multiple human malignancies.

Of particular interest is the detection of CRT expression on cancer stem cells, where it has been found that CRT expression segregates with tumorigenicity. Expression of CRT is used alone or in combination with other cancer stem cell markers, e.g. CD47, CD44, etc. to identify, target and/or isolated cancer stem cells.

BRIEF DESCRIPTION OF THE DRAWINGS

(FIG. 1B) A similar analysis as in A was performed for solid tumors (glioblastoma, n=9; transitional cell bladder carcinoma, n=8; serous papillary ovarian carcinoma, n=9) and normal human fetal tissues (neurons, n=3; astrocytes, n=6, bladder cells, n=6). ESA+ urothelium was analyzed for normal fetal bladder. Primary human bladder cancer patient samples and samples that had been passaged once in mice were used for profiling. (FIG. 1C and FIG. 1D) Cell surface calreticulin expression was determined on normal stem and progenitor cells, lymphocytes, and cancer stem and progenitor cells. Each symbol represents a different patient sample. Patient samples tested: NBM=10, AML=8, CML=13, bladder cancer=8, glioblastoma=8. NBM HSC=CD34+CD38-CD90+Lin–, AML LSC=CD34+CD38-CD90-Lin–, GMP=CD34+CD38+IL3rα+CD45RA+, CMP=CD34+CD38+IL3rα+CD45RA–. (FIG. 1E) Calreticulin expression did not differ between bulk and cancer stem cell populations for either bladder cancer (p=0.54) or glioblastoma (p=0.14). Bladder cancer CSC=CD44+Lin– (8), glioblastoma CSC=CD133+Lin– (22, 23). Annexin V-positive cells were excluded in the analysis of all samples.

(FIG. 2B) CD47 protein expression was determined by flow cytometry on Raji cells transduced with lentiviruses encoding shRNA CD47-knockdown constructs (shCD47) or controls. (FIG. 2C) Relative CD47 expression levels were quantified by comparing MFI to wild type Raji cells. (FIG. 2D) Raji cell clones were incubated with human macrophages in media alone or with CRT blocking peptide for 2 hours, after which phagocytosis was analyzed by fluorescence microscopy. Knockdown of CD47 in Raji cells (shCD47-1,-2) resulted in increased phagocytosis compared to untransduced Raji cells. No difference in phagocytosis was observed between untransduced and GAPD control-transduced Raji cells (p=0.45) Blockade of calreticulin on CD47-knockdown Raji cells completely abrogated phagocytosis. (FIG. 2E) MOLM-13 cells, a CD47-deficient human AML cell line, were incubated with human macrophages for two hours with the indicated peptides and monitored for phagocytosis as above. Significant phagocytosis was observed with IgG1 isotype control, while blockade of calreticulin or LRP reduced levels of phagocytosis (p=0.03 and p=0.01, respectively). Conditions were performed in triplicate; data presented as mean±SD. *p<0.05, p<0.005, *p<0.0005 (2-tailed Student's t-test).

(FIG. 3B) Cells from several normal human tissue types were incubated with human macrophages in the presence of the indicated antibodies and monitored for phagocytosis. No difference in phagocytosis was detected between IgG1 isotype control and anti-CD47 antibody incubation ($p=0.77$). (FIG. 3C) Primary human cancer cells were incubated with human macrophages in the presence of the indicated antibodies/peptides for two hours and monitored for phagocytosis. Each data point represents a different patient sample. Compared to IgG1 isotype control, incubation with anti-CD47 antibody enabled phagocytosis of cancer cells ($p<0.0001$) while incubation with calreticulin blocking peptide ($p=0.37$) or RAP, an LRP inhibitor ($p=0.67$), did not enable phagocytosis. In the presence of anti-CD47 antibody, incubation of cancer cells with either calreticulin blocking peptide or RAP completely abrogated anti-CD47 antibody-mediated phagocytosis ($p=0.77$ and $p=0.16$, respectively compared to IgG1 isotype control). *****$p<0.00001$ (2-sided Student's t-test). (FIG. 3D) A positive correlation was observed between cell surface CRT expression and degree of anti-CD47 antibody mediated phagocytosis (Pearson's correlation coefficient is shown). Each point represents a distinct patient sample that was incubated in the same in vitro phagocytosis assay. (FIG. 3E) Human NBM cells were incubated with human macrophages in the presence of the indicated antibodies or protein. Exogenous CRT enabled increased phagocytosis of NBM cells compared to vehicle control ($p=0.05$). No difference in phagocytosis was observed between IgG1 isotype control and anti-CD47 antibody ($p=0.49$). Conditions were performed in triplicate; data presented as mean±SD.

(FIG. 5B) 5,000 CRT− or CRT+ AML LSC were transplanted into the facial vein of sublethally-irradiated newborn NSG. Eight weeks later mice were sacrificed and analyzed for AML bone marrow engraftment. Equal AML engraftment (as shown by human CD45+ chimerism) was observed in both CRT− and CRT+ AML LSC. Representative data are shown. (FIG. 5C) CRT− and CRT+ primary human bladder cancer cells from mouse xenografts were sorted by FACS to >99% purity. (FIG. 5D,5E) 10,000 CRT− or CRT+ bladder cancer cells were transplanted subcutaneously onto the flanks of NSG mice. Eight weeks later solid tumor growth was equal in mice transplanted with CRT− and CRT+ cells (FIG. 5D, top panels). CRT+ and CRT-tumors were excised (FIG. 5D, bottom panels), with no difference in tumor weight (FIG. 5E, $p=0.63$).

(FIG. 6A) A positive correlation between cell surface CRT and ERp57 expression was found on primary human tumors or cancer cell lines using Pearson's correlation coefficient. (FIG. 6B) These cells were analyzed for cell surface expression on ERp57, CRT, and CD47 by flow cytometry. A representative staining profile is shown for Raji cells. A greater percentage of CRT positive cells expressed ERp57 (third panel) compared to CRT negative cells (second panel). CRT+ERp57+ cells also expressed CD47 (fourth panel) in similar levels to the bulk cell population (data not shown). (FIG. 6C) Cell surface ERp57 expression was quantified in CRT+ and CRT− cell populations from several tumor types. A greater percentage of CRT+ cells expressed ERp57 compared to CRT− counterparts ($p=0.0006$). Each symbol represents a distinct tumor sample. Samples shown were from patient samples or the following cell lines: blue square=Jurkat, green inverted triangle=Raji, green diamond=SUDHL4. All cells profiled in (FIG. 6A-6C) were excluded for annexin V-positive cells.

FIGS. 7A-7B. Live calreticulin positive cells from normal human tissues have higher levels of CD47 compared to calreticulin negative cells. (FIG. 7A,7B) Left panel: bulk normal human bone marrow cells (FIG. 7A) or normal human fetal bladder (ESA positive) urothelial cells (FIG. 7B) were profiled for cell surface calreticulin expression by flow cytometry. Right panel: cell surface calreticulin-negative and -positive cells were profiled for CD47 expression, demonstrating higher CD47 expression on calreticulin-positive cells. Annexin V-positive cells were excluded from the analysis of both bulk normal human bone marrow cells and fetal bladder cells. Data is representative of several samples.

(FIG. 9A-9B) CD47 expression was determined by flow cytometry on normal human hematopoietic cells (FIG. 9A) and fetal tissue cells (FIG. 9B) demonstrating expression on all normal cells profiled. Flow cytometry plots are from a representative sample of each normal tissue cell type.

(FIG. 10A) Cell surface CRT and CD47 expression was determined by flow cytometry on Jurkat cells, a T cell leukemia cell line. (FIG. 10B) Jurkat cells were incubated with human macrophages in the presence of the indicated antibodies and blocking peptides, and phagocytosis was determined by fluorescence microscopy. Anti-CD47 antibody was used at 10 μg/ml. CRT blocking peptide concentrations are shown as μg/ml. Each condition was performed in triplicate. Data is expressed as mean±SD.

FIGS. 11A-11D. Model for the integration of pro (CRT)- and anti (CD47)-phagocytic signals on normal and tumor cells at steady state and during anti-CD47 antibody therapy. (FIG. 11A,11B) At steady state, tumor, normal, and damaged cells express varying levels of cell surface CD47 and CRT, and it is the integration of both signals that determines whether the target cell will be phagocytosed. Tumor cells express CRT, but also higher levels of CD47 that delivers a dominant negative phagocytic signal (minus sign), leading to evasion of phagocytosis. In contrast, normal cells express lower levels of CD47, but do not express CRT, and thus no phagocytosis occurs. Lastly, damaged or apoptotic cells exhibit high levels of CRT expression, and this positive phagocytic signal (plus sign) dominates over low CD47 expression, leading to phagocytosis (dashed arrow). (FIG. 11C,11D) During anti-CD47 antibody therapy, the negative phagocytic stimulus (CD47) is blocked. In tumor cells, this unmasks the positive phagocytic signal (CRT), leading to phagocytosis. In contrast, normal cells are not phagocytosed since the positive phagocytic stimulus (CRT) is absent.

(FIG. 14A) Molm 13 cells (human acute myeloma cells) treated with apoptotic agent staurosporine express calreticulin. Live cells were stained with anti-calreticulin (CRT) antibody conjugated by a fluorophore. Histrograms represent an increase in cell surface calreticulin compared to isotype control, analyzed by flow cytometry. (FIG. 14B) Molm 13 cells treated with apoptotic agent staurosporine bind to LRP1 cluster IV-Fc protein. Live cells were stained with LRP1 cluster IV-Fc protein followed by a secondary anti-Fc antibody conjugated to a fluorophore. Histrograms represent an increase in the binding of LRP1 cluster IV-Fc protein. This binding can be blocked with calreticulin blocking peptide (CRT BP) and with an LRP1 inhibitor, receptor associated protein (RAP).

DETAILED DESCRIPTION OF THE EMBODIMENTS

Figure 1A:
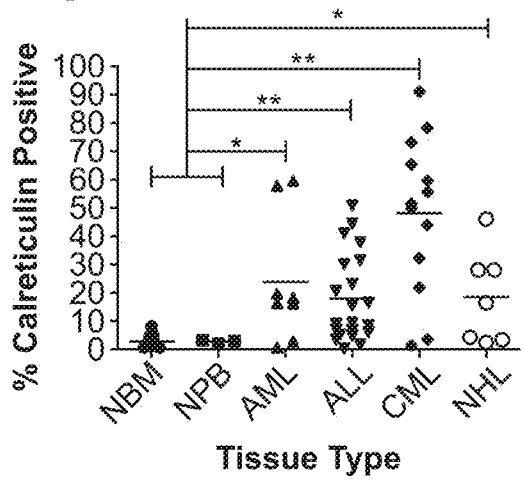
FIGS. 1A-1E. Cell surface calreticulin is expressed on cancer, but not normal, stem and progenitor cells (FIG. 1A) Cell surface calreticulin expression was determined by flow cytometry on primary human patient samples from several hematologic cancer types and normal cell counterparts including normal bone marrow (NBM, n=9), normal peripheral blood (NPB, n=3), acute myeloid leukemia (AML, n=8), acute lymphoblastic leukemia (ALL, n=21), chronic myeloid leukemia (CML, n=13), and non-Hodgkin lymphoma (NHL, n=7).

Under normal physiologic conditions, cellular homeostasis is partly regulated by balancing pro- and anti-phagocytic signals. For example, the anti-phagocytic protein CD47 is highly expressed on several human cancers including acute myeloid leukemia, non-Hodgkin lymphoma, and bladder cancer, where it allows cancer cells to evade phagocytosis by the innate immune system. It has been found that blockade of CD47 enables phagocytosis of cancer cells and leads to in vivo tumor elimination. In order for these target cells to be phagocytosed upon blockade of an anti-phagocytic signal, it is shown herein that the cells must also display a pro-phagocytic signal, which is identified as calreticulin. CRT is highly expressed on the cell surface of multiple human cancers, including without limitation, acute myeloid and lymphoblastic leukemias, chronic myeloid leukemia, non-Hodgkin lymphoma (NHL), bladder cancer, glioblastoma, and ovarian cancer, but minimally expressed on most normal cells.

Increased CD47 expression was found to be correlated with high calreticulin levels on cancer cells, and was necessary for protection from calreticulin-mediated phagocytosis. Phagocytosis induced by anti-CD47 antibody required the interaction of target cell calreticulin with its receptor low density lipoprotein-receptor related protein (LRP) on phagocytic cells, as blockade of the calreticulin/LRP interaction prevented anti-CD47 antibody mediated phagocytosis. Increased calreticulin expression is an adverse prognostic factor in diverse tumors including neuroblastoma, bladder cancer, and NHL.

Methods are provided to manipulate phagocytosis of cells, particularly cancer cells and hematopoietic cells, by modulating CRT activity. Methods are additionally provided for detection and monitoring of cancer cells by determining expression of CRT; where such cancer cells may be selectively targeted for ADCC, chemotherapy, etc. by agents that specifically bind CRT.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Calreticulin. Calreticulin is a multifunctional protein of 417 amino acids, molecular weight 48 kDa, that binds $Ca^{2+}$ ions, rendering it inactive. The $Ca^{2+}$ is bound with low affinity, but high capacity, and can be released on a signal. Calreticulin can be located in storage compartments associated with the endoplasmic reticulum, where it binds to misfolded proteins and prevents them from being exported to the Golgi apparatus. Calreticulin is also found in the nucleus, suggesting that it may have a role in transcription regulation. Calreticulin binds to the synthetic peptide KLGFFKR (SEQ ID NO: 1), which is almost identical to an amino acid sequence in the DNA-binding domain of the superfamily of nuclear receptors.

The gene symbol for calreticulin is CALR, and the human sequences may be accessed at Pubmed as follows: Protein Accession #NP_004334; Nucleotide Accession #: NM_004343.

Gardai et al. (2005) stated that calreticulin on the surface of apoptotic cells serves as a recognition and clearance ligand by activating the internalization receptor LRP on the responding phagocyte cell surface. Using mouse and human cells, it was found that the surface expression of calreticulin increased and calreticulin was redistributed during apoptosis, possibly enhancing stimulation of LRP on the phagocyte. In addition, CD47 on the apoptotic cell surface was altered and/or lost, which reduced the activation of SIRP-alpha on the phagocytic cell surface, resulting in phagocytosis.

In CT26 mouse colon cancer cells, Obeid et al. (2007) demonstrated that anthracyclins induced immunogenic cell death by way of a rapid, pre-apoptotic translocation of calreticulin to the cell surface. Blockade or knockdown of CALR suppressed phagocytosis of anthracyclin-treated tumor cells by dendritic cells and abolished their immunogenicity in mice. Anthracyclin-induced CALR translocation was mimicked by inhibition of the protein phosphatase-1/Gadd34 complex. Administration of recombinant CALR or inhibitors of Pp1/Gadd34 restored immunogenicity of cell death elicited by etoposide and mitomycin C and enhanced their antitumor effects in vivo.

Low density lipoprotein receptor-related protein (LRP; CD91). The low density lipoprotein receptor-related protein (LRP) is a 4,544-amino acid protein containing a single transmembrane segment, with a high degree of sequence identity to the LDL receptor. GP96, HSP90, HSP70, and calreticulin use CD91 as a common receptor. The human genetic sequences may be accessed at Pubmed as follows: Nucleotide Accession #: NM_002332.2 GI:126012561.

Calreticulin binding agents. Agents that specifically bind to calreticulin (CRT) are of interest as detectable markers for imaging and diagnosis, as therapeutic agents for targeted delivery of chemotherapeutic moieties; as therapeutic agents for antibody dependent cytotoxicity (ADCC); as agonists for enhancing the pro-phagocytic activity of CRT; and as inhibitors of CRT activity, e.g. by blocking the interaction of CRT and LRP. The term "specific binding member" or "binding member" as used herein refers to a member of a specific binding pair, i.e. two molecules, usually two different molecules, where one of the molecules (i.e., first specific binding member) through chemical or physical means specifically binds to the other molecule (i.e., second specific binding member). CRT binding agents useful in the methods of the invention include analogs, derivatives and fragments of the original specific binding member, e.g. Fab fragments of antibodies, etc.

CRT binding agents that act as inhibitors include blocking peptides, which are commercially available and known in the art (see Urade et al. (2004) Biochemistry 43 (27), 8858-8868, herein specifically incorporated by reference; and commercial suppliers including, inter alia, Aviva Systems Biology; MBL International Corporation), including without limitation the peptides KLGFFKR (SEQ ID NO: 1); and KEEEEDKKRKEEEEAEDKEDDEDKDEDEEDEED-KEEDEEEDVPQA KDEL (SEQ ID NO: 2); blocking oligosaccharides (see Arai et al. (2005) Chembiochem 6(12): 2281-2289, herein specifically incorporated by reference); and blocking antibodies (see Urade et al., supra. and peptide sources).

In a preferred embodiment, the specific binding member is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies utilized in the present invention may be polyclonal antibodies, although monoclonal antibodies are preferred because they may be reproduced by cell culture or recombinantly, and can be modified to reduce their antigenicity.

The phrase "bispecific antibody" refers to a synthetic or recombinant antibody that recognizes more than one protein. Examples include bispecific antibodies 2B1, 520C9xH22, mDX-H210, and MDX447. Bispecific antibodies directed against a combination of epitopes, will allow for the targeting and/or depletion of cellular populations expressing the combination of epitopes. Exemplary bi-specific antibodies include those targeting a combination of CALRETICULIN and a cancer cell marker, such as, CD96, CD97, CD99, PTHR2, HAVCR2 etc. Generation of bi-specific antibody is described in the literature, for example, in U.S. Pat. Nos. 5,989,830, 5,798,229, which are incorporated herein by reference.

Polyclonal antibodies can be raised by a standard protocol by injecting a production animal with an antigenic composition. See, e.g., Harlow and Lane, Antibodies: A Laboratory Manual, Cold Spring Harbor Laboratory, 1988. When utilizing an entire protein, or a larger section of the protein, antibodies may be raised by immunizing the production animal with the protein and a suitable adjuvant (e.g., Freund's, Freund's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the protein target, a superior immune response may be elicited if the polypeptide is joined to a carrier protein, such as ovalbumin, BSA or KLH.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. In addition, the antibodies or antigen binding fragments may be produced by genetic engineering. Humanized, chimeric, or xenogeneic human antibodies, which produce less of an immune response when administered to humans, are preferred for use in the present invention.

Antibodies that have a reduced propensity to induce a violent or detrimental immune response in humans (such as anaphylactic shock), and which also exhibit a reduced propensity for priming an immune response which would prevent repeated dosage with the antibody therapeutic or imaging agent are preferred for use in the invention. These antibodies are preferred for all administrative routes. Thus, humanized, chimeric, or xenogenic human antibodies, which produce less of an immune response when administered to humans, are preferred for use in the present invention.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference). Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference. Alternatively, single chain antibodies (Fv, as described below) can be produced from phage libraries containing human variable regions. See U.S. Pat. No. 6,174,708, incorporated fully herein by reference.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ficin, pepsin, papain, or other protease cleavage. "Fragment" or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Fv fragments are heterodimers of the variable heavy chain domain ($V_H$) and the variable light chain domain ($V_L$). The heterodimers of heavy and light chain domains that occur in whole IgG, for example, are connected by a disulfide bond. Recombinant Fvs in which $V_H$ and $V_L$ are connected by a peptide linker are typically stable, see, for example, Huston et al., Proc. Natl. Acad, Sci. USA 85:5879-5883 (1988) and Bird et al., Science 242:423-426 (1988), both fully incorporated herein, by reference. These are single chain Fvs which have been found to retain specificity and affinity and have been shown to be useful for imaging tumors and to make recombinant immunotoxins for tumor therapy. Any of these minimal antibodies may be utilized in the present invention, and those which are humanized to avoid HAMA reactions are preferred for use in embodiments of the invention.

In addition, derivatized immunoglobulins with added chemical linkers, detectable moieties, e.g. fluorescent dyes, enzymes, radioisotopes, substrates, chemiluminescent moieties, or specific binding moieties, e.g. streptavidin, avidin, biotin, etc. may be utilized in the methods and compositions of the present invention. For convenience, the term "antibody" or "antibody moiety" will be used throughout to generally refer to molecules which specifically bind to an epitope of the targeted protein, although the term will encompass all immunoglobulins, derivatives, fragments, recombinant or engineered immunoglobulins, and modified immunoglobulins, as described above.

Candidate binding agents can be tested for activity by any suitable standard means. As a first screen, the antibodies may be tested for binding against the target antigen utilized to produce them. As a second screen, candidate agents may be tested for binding to an appropriate cell, e.g. cancer cell, hematopoietic cell, etc. For these screens, the candidate antibody may be labeled for detection (e.g., with fluorescein or another fluorescent moiety, or with an enzyme such as horseradish peroxidase). After selective binding to the target is established, the candidate agent may be tested for appropriate activity (i.e., the ability to decrease tumor cell growth and/or to aid in visualizing tumor cells) in an in vivo model.

The antibodies for use in the present invention may have utility without conjugation, e.g. when the native activity of the target protein is altered in the tumor cell, when the antibody binding is sufficient to activate ADCC, etc. Such antibodies, which may be selected as described above, may be utilized without further modification. However, the conjugation of cytotoxic or imaging agents is yet another preferred embodiment when utilizing these antibodies because the added moieties add functionality to the therapeutic.

Thus, in many preferred embodiments of the invention, the antibodies may be coupled or conjugated to one or more therapeutic cytotoxic or imaging moieties. As used herein, "cytotoxic moiety" simply means a moiety which inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof. As utilized herein, "imaging moiety" means a moiety which can be utilized to increase contrast between a tumor and the surrounding healthy tissue in a visualization technique (e.g., radiography, positron-emission tomography, magnetic resonance imaging, direct or indirect visual inspection). Thus, suitable imaging moieties include radiography moieties (e.g. heavy metals and radiation emitting moieties), positron emitting moieties, magnetic resonance contrast moieties, and optically visible moieties (e.g., fluorescent or visible-spectrum dyes, visible particles, etc.).

In general, therapeutic or imaging agents may be conjugated to the antibody by any suitable technique, with appropriate consideration of the need for pharmokinetic stability and reduced overall toxicity to the patient. A therapeutic agent may be coupled to a suitable antibody moiety either directly or indirectly (e.g. via a linker group). A direct reaction between an agent and an antibody is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer to distance an antibody from an agent in order to avoid interference with binding capabilities. A linker group can also serve to increase the chemical reactivity of a substituent on a moiety or an antibody, and thus increase the coupling efficiency. An increase in chemical reactivity may also facilitate the use of moieties, or functional groups on moieties, which otherwise would not be possible.

Where a cytotoxic moiety is more potent when free from the antibody portion of the immunoconjugates of the present invention, it may be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

Preferred radionuclides for use as cytotoxic moieties are radionuclides which are suitable for pharmacological administration. Such radionuclides include $^{123}I$, $^{125}I$, $^{131}I$, $^{90}Y$, $^{211}At$, $^{67}Cu$, $^{186}Re$, $^{188}Re$ $^{212}Pb$, and $^{212}Bi$. Preferred chemotoxic agents include small-molecule drugs such as carboplatin, cisplatin, vincristine, taxanes such as paclitaxel and docetaxel, hydroxyurea, gemcitabine, vinorelbine, irinotecan, tirapazamine, matrilysin, methotrexate, pyrimidine and purine analogs, and other suitable small toxins known in the art. Preferred chemotoxin differentiation inducers include phorbol esters and butyric acid. Chemotoxic moieties may be directly conjugated to the antibody moiety via a chemical linker, or may encapsulated in a carrier, which is in turn coupled to the antibody moiety. Preferred toxin proteins for use as cytotoxic moieties include ricins A and B, abrin, diphtheria toxin, bryodin 1 and 2, momordin, trichokirin, cholera toxin, gelonin, *Pseudomonas* exotoxin, *Shigella* toxin, pokeweed antiviral protein, and other toxin proteins known in the medicinal biochemistry arts.

Preferred radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the compositions and methods of the invention. Positron emitting moieties for use in the present invention include $^{18}F$, which can be easily conjugated by a fluorination reaction with the antibody. Magnetic resonance contrast moieties include chelates of chromium(III), manganese(II), iron(II), nickel(II), copper (II), praseodymium(III), neodymium(III), samarium(III) and ytterbium(III) ion. Optically visible moieties for use as imaging moieties include fluorescent dyes, or visible-spectrum dyes, visible particles, and other visible labeling moieties. Fluorescent dyes such as fluorescein, coumarin, rhodamine, bodipy Texas red, and cyanine dyes, are useful when sufficient excitation energy can be provided to the site to be inspected visually. Endoscopic visualization procedures may be more compatible with the use of such labels. Acceptable dyes include FDA-approved food dyes and colors, which are non-toxic, although pharmaceutically acceptable dyes which have been approved for internal administration are preferred.

In one embodiment of the invention, the agent, or a pharmaceutical composition comprising the agent, is provided in an amount effective to detectably inhibit the binding of calreticulin to LRP present on the surface of phagocytic cells. The effective amount is determined via empirical testing routine in the art. The effective amount may vary depending on the number of cells being transplanted, site of transplantation and factors specific to the transplant recipient.

Calreticulin "mimetics" and "agonists" include molecules that function similarly to or potentiate CRT by binding and activating LRP receptor. Molecules useful as CRT mimetics include derivatives, variants, and biologically active fragments of naturally occurring CRT. Molecules useful as agonists include antibodies and other agents that act to enhance the pro-phagocytic activity of CRT.

A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%. The variant polypeptides can be naturally or non-naturally glycosylated, i.e., the polypeptide has a glycosylation pattern that differs from the glycosylation pattern found in the corresponding naturally occurring protein. The variant polypeptides can have post-translational modifications not found on the natural CRT protein.

Fragments of soluble CRT, particularly biologically active fragments and/or fragments corresponding to functional domains, are of interest. Fragments of interest will typically be at least about 10 aa to at least about 15 aa in length, usually at least about 50 aa in length, but will usually not exceed about 142 aa in length, where the fragment will have a stretch of amino acids that is identical to CRT. A fragment "at least 20 aa in length," for example, is intended to include 20 or more contiguous amino acids from, for example, the polypeptide encoded by a cDNA for CRT. In this context "about" includes the particularly recited value or a value larger or smaller by several (5, 4, 3, 2, or 1) amino acids. The protein variants described herein are encoded by polynucleotides that are within the scope of the invention. The genetic code can be used to select the appropriate codons to construct the corresponding variants. The polynucleotides may be used to produce polypeptides, and these polypeptides may be used to produce antibodies by known methods.

A "fusion" polypeptide is a polypeptide comprising a polypeptide or portion (e.g., one or more domains) thereof fused or bonded to heterologous polypeptide. A fusion soluble CRT protein, for example, will share at least one biological property in common with a native sequence soluble CRT polypeptide. Examples of fusion polypeptides include immunoadhesins, as described above, which combine a portion of the CRT polypeptide with an immunoglobulin sequence, including an immunoglobulin specific for CD47, and epitope tagged polypeptides, which comprise a soluble CRT polypeptide or portion thereof fused to a "tag polypeptide". The tag polypeptide has enough residues to provide an epitope against which an antibody can be made, yet is short enough such that it does not interfere with biological activity of the CRT polypeptide. Suitable tag polypeptides generally have at least six amino acid residues and usually between about 6-60 amino acid residues.

A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. The term "derivative" encompasses both amino acid sequence variants of polypeptide and covalent modifications thereof. Derivatives and fusion of soluble CRT find use as CRT mimetic molecules.

In vitro assays for calreticulin biological activity include, e.g. phagocytosis of porcine cells by human macrophages, binding to LRP, etc. A candidate agent useful as a calreticulin agonist mimetic results in the down regulation of phagocytosis by at least about 10%, at least about 20%, at least about 50%, at least about 70%, at least about 80%, or up to about 90% compared to level of phagocytosis observed in absence of candidate agent.

A plurality of assays may be run in parallel with different concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in binding.

By "manipulating phagocytosis" is meant an up-regulation or a down-regulation in phagocytosis by at least about 10%, or up to 20%, or 50%, or 70% or 80% or up to about 90% compared to level of phagocytosis observed in absence of intervention. Thus in the context of decreasing phagocytosis of circulating hematopoietic cells, particularly in a transplantation context, manipulating phagocytosis means a down-regulation in phagocytosis by at least about 10%, or up to 20%, or 50%, or 70% or 80% or up to about 90% compared to level of phagocytosis observed in absence of intervention.

The terms "phagocytic cells" and "phagocytes" are used interchangeably herein to refer to a cell that is capable of phagocytosis. There are three main categories of phagocytes: macrophages, mononuclear cells (histiocytes and monocytes); polymorphonuclear leukocytes (neutrophils) and dendritic cells.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

Hematopoietic stem cells (HSC), as used herein, refers to a population of cells having the ability to self-renew, and to give rise to all hematopoietic lineages. Such cell populations have been described in detail in the art. Hematopoietic progenitor cells include the myeloid committed progenitors (CMP), the lymphoid committed progenitors (CLP), megakaryocyte progenitors, and multipotent progenitors. The earliest known lymphoid-restricted cell in adult mouse bone marrow is the common lymphocyte progenitor (CLP), and the earliest known myeloid-restricted cell is the common myeloid progenitor (CMP). Importantly, these cell populations possess an extremely high level of lineage fidelity in in vitro and in vivo developmental assays. A complete description of these cell subsets may be found in Akashi et al. (2000) Nature 404(6774):193, U.S. Pat. No. 6,465,247; and published application U.S. Ser. No. 09/956,279 (common myeloid progenitor); Kondo et al. (1997) Cell 91(5):661-7, and International application WO99/10478 (common lymphoid progenitor); and is reviewed by Kondo et al. (2003) Annu Rev Immunol. 21:759-806, each of which is herein specifically incorporated by reference. The composition may be frozen at liquid nitrogen temperatures and stored for long periods of time, being capable of use on thawing. For such a composition, the cells will usually be stored in a 10% DMSO, 50% FCS, 40% RPMI 1640 medium.

Populations of interest for use in the methods of the invention include substantially pure compositions, e.g. at least about 50% HSC, at least about 75% HSC, at least about 85% HSC, at least about 95% HSC or more; or may be combinations of one or more stem and progenitor cells populations, e.g. white cells obtained from apheresis, etc. Where purified cell populations are desired, the target population may be purified in accordance with known techniques. For example, a population containing white blood cells, particularly including blood or bone marrow samples, are stained with reagents specific for markers present of hematopoietic stem and progenitor cells, which markers are sufficient to distinguish the major stem and progenitor groups. The reagents, e.g. antibodies, may be detectably labeled, or may be indirectly labeled in the staining procedure.

Any combination of markers may be used that are sufficient to select for the stem/progenitor cells of interest. A marker combination of interest may include CD34 and CD38, which distinguishes hematopoietic stem cells, (CD34$^+$, CD38$^-$) from progenitor cells, which are CD34$^+$, CD38$^+$). HSC are lineage marker negative, and positive for expression of CD90.

In the myeloid lineage are three cell populations, termed CMPs, GMPs, and MEPs. These cells are CD34$^+$ CD38$^+$, they are negative for multiple mature lineage markers including early lymphoid markers such as CD7, CD10, and IL-7R, and they are further distinguished by the markers CD45RA, an isoform of CD45 that can negatively regulate at least some classes of cytokine receptor signaling, and IL-3R. These characteristics are CD45RA$^-$ IL-3R$\alpha^{lo}$ (CMPs), CD45RA$^+$IL-3R$\alpha^{lo}$ (GMPs), and CD45RA$^-$ IL-3R$\alpha^-$ (MEPs). CD45RA$^-$ IL-3R$\alpha^{lo}$ cells give rise to GMPs and MEPs and at least one third generate both GM and MegE colonies on a single-cell level. All three of the myeloid lineage progenitors stain negatively for the markers Thy-1 (CD90), IL-7R$\alpha$ (CD127); and with a panel of lineage markers, which lineage markers may include CD2; CD3; CD4; CD7; CD8; CD10; CD11 b; CD14; CD19; CD20; CD56; and glycophorin A (GPA) in humans and CD2; CD3; CD4; CD8; CD19; IgM; Ter110; Gr-1 in mice. With the exception of the mouse MEP subset, all of the progenitor cells are CD34 positive. In the mouse all of the progenitor subsets may be further characterized as Sca-1 negative, (Ly-6E and Ly-6A), and c-kit high. In the human, all three of the subsets are CD38$^+$.

Common lymphoid progenitors, CLP, express low levels of c-kit (CD117) on their cell surface. Antibodies that specifically bind c-kit in humans, mice, rats, etc. are known in the art. Alternatively, the c-kit ligand, steel factor (Slf) may be used to identify cells expressing c-kit. The CLP cells express high levels of the IL-7 receptor alpha chain (CDw127). Antibodies that bind to human or to mouse CDw127 are known in the art. Alternatively, the cells are identified by binding of the ligand to the receptor, IL-7. Human CLPs express low levels of CD34. Antibodies specific for human CD34 are commercially available and well known in the art. See, for example, Chen et al. (1997) *Immunol Rev* 157:41-51. Human CLP cells are also characterized as CD38 positive and CD10 positive. The CLP subset also has the phenotype of lacking expression of lineage specific markers, exemplified by B220, CD4, CD8, CD3, Gr-1 and Mac-1. The CLP cells are characterized as lacking expression of Thy-1, a marker that is characteristic of hematopoietic stem cells. The phenotype of the CLP may be further characterized as Mel-14$^-$, CD43$^{lo}$, HSA$^{lo}$, CD45$^+$ and common cytokine receptor $\gamma$ chain positive.

Megakaryocyte progenitor cells (MKP) cells are positive for CD34 expression, and tetraspanin CD9 antigen. The CD9 antigen is a 227-amino acid molecule with 4 hydrophobic domains and 1 N-glycosylation site. The antigen is widely expressed, but is not present on certain progenitor cells in the hematopoietic lineages. The MKP cells express CD41, also referred to as the glycoprotein IIb/IIIa integrin, which is the platelet receptor for fibrinogen and several other extracellular matrix molecules, for which antibodies are commercially available, for example from BD Biosciences, Pharmingen, San Diego, Calif., catalog number 340929, 555466. The MKP cells are positive for expression of CD117, which recognizes the receptor tyrosine kinase c-Kit. Antibodies are commercially available, for example from BD Biosciences, Pharmingen, San Diego, Calif., Cat. No. 340529. MKP cells are also lineage negative, and negative for expression of Thy-1 (CD90).

The phrase "solid tumor" as used herein refers to an abnormal mass of tissue that usually does not contain cysts or liquid areas. Solid tumors may be benign or malignant. Different types of solid tumors are named for the type of cells that form them. Examples of solid tumors are sarcomas, carcinomas, lymphomas etc.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "recipient", "individual", "subject", "host", and "patient", used interchangeably herein and refer to any mammalian subject for whom diagnosis, treatment, or therapy is desired, particularly humans.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The terms "cancer", "neoplasm", "tumor", and "carcinoma", "leukemia" are used interchangeably herein to refer to cells which exhibit relatively autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. Detection of cancerous cells is of particular interest. The term "normal" as used in the context of "normal cell," is meant to refer to a cell of an untransformed phenotype or exhibiting a morphology of a non-transformed cell of the tissue type being examined. "Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

"Therapeutic target" refers to a gene or gene product that, upon modulation of its activity (e.g., by modulation of expression, biological activity, and the like), can provide for modulation of the cancerous phenotype. As used throughout, "modulation" is meant to refer to an increase or a decrease in the indicated phenomenon (e.g., modulation of a biological activity refers to an increase in a biological activity or a decrease in a biological activity).

Diagnosis and Imaging of Cancer

Detection of calreticulin expression, e.g. cell surface protein, mRNA, etc., particularly cell surface protein, is used alone or in conjunction with CD47 expression for clinical diagnostic applications including primary diagnosis of cancers, monitoring of interval disease progression, and monitoring of minimal residual disease status, including without limitation hematopoietic malignancies including acute myelogenous leukemia (AML), chronic myelogenous leukemia (CML), acute lymphocytic leukemia (ALL); and non-Hodgkin lymphoma (NHL) as well as solid tumors including but not limited to bladder, ovarian, brain cancers, and other epithelial cancers. Cancer stem cells of interest also include carcinomas, e.g. squamous cell carcinoma, ovarian carcinoma, etc.; glioblastomas, and the like. Of interest is included the detection and treatment of cells prior to chemotherapeutic treatment.

In a related embodiment, an agent that selectively binds to CRT, e.g. soluble LRP, anti-CTR antibody, etc. is labeled with a detectable moiety, e.g. a fluorophore, imaging radioisotope, etc. for clinical diagnostic imaging applications including primary diagnosis of cancers, monitoring of interval disease progression, and monitoring of minimal residual disease status. Imaging may be performed in vivo or ex vivo.

Detection of CTR expression is also used in prognosis of cancer, where increased levels of CTR are shown to be associated with a worse clinical prognosis in multiple human malignancies.

Of particular interest is the detection of CRT expression on cancer stem cells, where it has been found that CRT expression segregates with tumorigenicity. Expression of CRT is used alone or in combination with other cancer stem cell markers, e.g. CD47, CD44, etc. to identify, target and/or isolated cancer stem cells.

Binding agents specific for CRT, e.g. antibodies, may be utilized for immunophenotyping of cells and biological samples. Monoclonal antibodies directed against a specific epitope, or combination of epitopes, will allow for the screening of cellular populations expressing the CRT. Various techniques can be utilized using monoclonal antibodies to screen for cellular populations expressing CRT, and include magnetic separation using antibody-coated magnetic beads, "panning" with antibody attached to a solid matrix (i.e., plate), and flow cytometry (See, e.g., U.S. Pat. No. 5,985,660; and Morrison et al. Cell, 96:737-49 (1999)). These techniques allow for the screening of particular populations of cells; in immunohistochemistry of biopsy samples; in detecting the presence of markers shed by cancer cells into the blood and other biologic fluids, and the like.

The presence of CRT in a patient sample can be indicative of the stage of the cancer. In addition, detection of CRT can be used to monitor response to therapy and to aid in prognosis. The presence of CRT can be utilized for quantitating the cells having the phenotype of the stem cell. In addition to cell surface phenotyping, it may be useful to quantitate the cells in a sample that have a "stem cell" character, which may be determined by functional criteria, such as the ability to self-renew, to give rise to tumors in vivo, e.g. in a xenograft model, and the like.

Clinical samples for use in the methods of the invention may be obtained from a variety of sources, particularly blood and tumor biopsy samples, although in some instances samples such as bone marrow, lymph, cerebrospinal fluid, synovial fluid, and the like may be used. Such samples can be separated by centrifugation, elutriation, density gradient separation, apheresis, affinity selection, panning, FACS, centrifugation with Hypaque, etc. prior to analysis, and usually a mononuclear fraction (PBMC) will be used. Once a sample is obtained, it can be used directly, frozen, or maintained in appropriate culture medium for short periods of time. Various media can be employed to maintain cells. The samples may be obtained by any convenient procedure, such as the drawing of blood, venipuncture, biopsy, or the like. Usually a sample will comprise at least about $10^2$ cells, more usually at least about $10^3$ cells, and preferable $10^4$, $10^5$ or more cells. Typically the samples will be from human patients, although animal models may find use, e.g. equine, bovine, porcine, canine, feline, rodent, e.g. mice, rats, hamster, primate, etc.

An appropriate solution may be used for dispersion or suspension of the cell sample. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Analysis of the cell staining will use conventional methods. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The CRT affinity reagents may be antibodies, specific receptors or ligands for the cell surface molecules indicated above. In addition to antibody reagents, peptide-MHC antigen and T cell receptor pairs may be used; peptide ligands and receptors; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeled cells are then quantitated as to the expression of cell surface markers. The comparison of a differential analysis obtained from a patient sample, and a reference differential progenitor analysis is accomplished by the use of suitable deduction protocols, AI systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. at initial diagnosis of cancer, following therapy, etc. The methods of the invention allow early therapeutic intervention, e.g. initiation of chemotherapy or antibody mediated therapy, increase of dose, changing selection of drugs, and the like.

In another embodiment, methods are provided for targeting or depleting cancer stem cells, the method comprising contacting a population of cells, e.g. blood from a cancer patient, with a reagent that specifically binds CTR in order to target or deplete the cancer stem cells. In certain aspects, the reagent is an antibody conjugated to a cytotoxic agent, e.g. radioactive isotope, chemotherapeutic agent, toxin, etc. In some embodiments, the depletion is performed on an ex vivo population of cells, e.g. the purging of autologous stem cell products (mobilized peripheral blood or bone marrow) for use in autologous transplantation for cancer patients.

In some embodiments of the invention, the number of cancer stem cells (CSC), which express CRT, in a patient sample is determined relative to the total number of cancer cells, where a greater percentage of CSC is indicative of the potential for continued self-renewal of cells with the cancer phenotype. The quantitation involves detection of CRT expression, and may further utilize expression of other markers known to be found on CSC, including upregulated CD47, CD44, markers of AML and CML LSC, and the like. The quantitation of CSC in a patient sample may be compared to a reference population, e.g. a patient sample such as a blood sample, a remission patient sample, etc. In some embodiments, the quantitation of CSC is performed during the course of treatment, where the number of cancer cells and the percentage of such cells that are CSC are quantitated before, during and as follow-up to a course of therapy. Desirably, therapy targeted to cancer stem cells results in a decrease in the total number, and/or percentage of CSC in a patient sample.

In other embodiments of the invention, anti-cancer agents are targeted to CSC by specific binding to CRT, or a combination of CRT and a second marker, including CD47. In such embodiments, the anti-cancer agents include antibodies and antigen-binding derivatives thereof specific for a marker or combination of markers of the present invention, which are optionally conjugated to a cytotoxic moiety. Depletion of CSC is therapeutically useful. Depletion achieves a reduction in circulating CSC by up to about 30%, or up to about 40%, or up to about 50%, or up to about 75% or more. Depletion can be achieved by using an agent to deplete CSC either in vivo or ex vivo.

The CSC are identified by their phenotype with respect to particular markers, and/or by their functional phenotype. In some embodiments, the CSC are identified and/or isolated by binding to the cell with reagents specific for the markers of interest. The cells to be analyzed may be viable cells, or may be fixed or embedded cells. In some embodiments, the reagents specific for the markers of interest are antibodies, which may be directly or indirectly labeled. Such antibodies will usually include antibodies specific for a marker or combination of markers of the present invention.

A cancer, including without limitation AML, ALL, CML, etc. can be staged by analysis of the presence of cancer stem cells. Staging is useful for prognosis and treatment. In one embodiment of the invention, a sample from a leukemia patient is stained with reagents specific for a marker or combination of markers of the present invention. The analysis of staining patterns provides the relative distribution of CSC, which distribution predicts the stage of leukemia. In some embodiments, the sample is analyzed by histochemistry, including immunohistochemistry, in situ hybridization, immunofluorescence and the like, for the presence of $CD34^+$ $CD38^-$ cells that express a marker or combination of markers of the present invention. The presence of such cells indicates the presence of CSC. In one embodiment, the patient sample is compared to a control, or a standard test value. In another embodiment, the patient sample is compared to a pre-leukemia sample, or to one or more time points through the course of the disease. Samples, including tissue sections, slides, etc. are stained with reagents specific for markers that indicate the presence of cancer stem cells. Samples may be frozen, embedded, present in a tissue microarray, and the like. The reagents, e.g. antibodies, polynucleotide probes, etc. may be detectably labeled, or may be indirectly labeled in the staining procedure.

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analysis, proteomics, cell surface staining, or other means, in order to determine the presence of markers that are useful in classification. For example, genetic abnormalities can be causative of disease susceptibility or drug responsiveness, or can be linked to such phenotypes.

Depletion of CSC is useful in the treatment of cancer. Depletion can be achieved by several methods. Depletion is defined as a reduction in the target population by up to about 30%, or up to about 40%, or up to about 50%, or up to about 75% or more. An effective depletion is usually determined by the sensitivity of the particular disease condition to the levels of the target population. Thus in the treatment of certain conditions a depletion of even about 20% could be beneficial.

A CRT specific agent that specifically depletes the targeted CSC is used to contact the patient in vitro or in vivo, wherein after the contacting step, there is a reduction in the number of viable CSC in the targeted population. An effective dose of antibodies for such a purpose is sufficient to decrease the targeted population to the desired level, for example as described above. Antibodies for such purposes may have low antigenicity in humans or may be humanized antibodies.

In one embodiment of the invention, antibodies for depleting target population are added to patient blood in vivo. In another embodiment, the antibodies are added to the patient blood ex vivo. Beads coated with the antibody of interest can be added to the blood, target cells bound to these beads can then be removed from the blood using procedures common in the art. In one embodiment the beads are magnetic and are removed using a magnet. Alternatively, when the antibody is biotinylated, it is also possible to indirectly immobilize the antibody onto a solid phase which has adsorbed avidin, streptavidin, or the like. The solid phase, usually agarose or sepharose beads are separated from the blood by brief centrifugation. Multiple methods for tagging antibodies and removing such antibodies and any cells bound to the antibodies are routine in the art. Once the desired degree of depletion has been achieved, the blood is returned to the patient. Depletion of target cells ex vivo decreases the side effects such as infusion reactions associated with the intravenous administration. An additional advantage is that the repertoire of available antibodies is expanded significantly as this procedure does not have to be limited to antibodies with low antigenicity in humans or humanized antibodies.

In vitro, CSC may be separated from a complex mixture of cells by techniques that enrich for cells that differentially express CRT or combination of markers of the present invention. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for CSC are achieved in this manner. The subject population may be at or about 50% or more of the cell composition, and preferably be at or about 75% or more of the cell composition, and may be 90% or more. The desired cells are identified by their surface phenotype, by the ability to self-renew, ability to form tumors, etc. The enriched cell population may be used immediately, or may be frozen at liquid nitrogen temperatures and stored for long periods of time, being thawed and capable of being reused. The cells may be stored in 10% DMSO, 90% FCS medium. The population of cells enriched for CSC may be used in a variety of screening assays and cultures, as described below.

The enriched CSC population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

In some embodiments of the invention, the expression of CRT on cancer cells, including without limitation cancer cells prior to treatment with a chemotherapeutic drug, is utilized to enhance killing of the cancer cells. Cancer cells can be contacted with an agonist of CRT, e.g. an agonistic antibody, particularly one that activates LRP, in the presence of phagocytic cells in order to enhance phagocytosis of the cancer cells. Cancer cells can also be contacted with an antibody to CRT that eliminates cancer cells by ADCC, complement, and other Fc-receptor mediated effects. In some such embodiments, the CRT agonist is administered in combination with an agent that blocks CD47 signaling, e.g. soluble SIRPα, anti-CD47, and the like. Included in such agents are bi-specific antibodies targeted to both CD47 and CRT or CD47 and LRP. Also included are agents comprising a CD47 blocking moiety and an active portion of CTR protein.

In related embodiments, cancer cells, including without limitation cancer cells prior to treatment with a chemotherapeutic drug, are contacted with an agent that selectively binds to CRT, including antibodies, soluble LRP, etc., which agent is optionally conjugated to a toxic moiety, e.g. a radionuclide, toxin, etc. to induce killing of the cell to which the agent has bound.

"Reducing growth of cancer cells" includes, but is not limited to, reducing proliferation of cancer cells, and reducing the incidence of a non-cancerous cell becoming a cancerous cell. Whether a reduction in cancer cell growth has been achieved can be readily determined using any known assay, including, but not limited to, [$^3$H]-thymidine incorporation; counting cell number over a period of time; detecting and/or measuring a marker associated with the cancer, etc.

Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood of the individual. The substance can be administered systemically or locally, usually systemically.

As an alternative embodiment, an agent, e.g. a chemotherapeutic drug that reduces cancer cell growth, can be targeted to a cancer cell by conjugation to a CTR specific antibody. Thus, in some embodiments, the invention provides a method of delivering a drug to a cancer cell, comprising administering a drug-antibody complex to a subject, wherein the antibody is specific for CTR, and the drug is one that reduces cancer cell growth, a variety of which are known in the art. Targeting can be accomplished by coupling (e.g., linking, directly or via a linker molecule, either covalently or non-covalently, so as to form a drug-antibody complex) a drug to an antibody specific for a cancer-associated polypeptide.

In certain embodiments, a bi-specific antibody may be used. For example a bi-specific antibody in which one antigen binding domain is directed against CTR and the other antigen binding domain is directed against a cancer cell marker, such as CD47, CD96, CD97, CD99, PTHR2, HAVCR2 etc.

For administration, the antibody-therapeutic or antibody-imaging agent will generally be mixed, prior to administration, with a non-toxic, pharmaceutically acceptable carrier substance. Usually, this will be an aqueous solution, such as normal saline or phosphate-buffered saline (PBS), Ringer's solution, lactate-Ringer's solution, or any isotonic physiologically acceptable solution for administration by the chosen means. Preferably, the solution is sterile and pyrogen-free, and is manufactured and packaged under current Good Manufacturing Processes (GMPs), as approved by the FDA. The clinician of ordinary skill is familiar with appropriate ranges for pH, tonicity, and additives or preservatives when formulating pharmaceutical compositions for administration by intravascular injection, intrathecal injection, injection into the cerebro-spinal fluid, direct injection into the tumor, or by other routes. In addition to additives for adjusting pH or tonicity, the antibody-therapeutics and antibody-imaging agents may be stabilized against aggregation and polymerization with amino acids and non-ionic detergents, polysorbate, and polyethylene glycol. Optionally, additional stabilizers may include various physiologically-acceptable carbohydrates and salts. Also, polyvinylpyrrolidone may be added in addition to the amino acid. Suitable therapeutic immunoglobulin solutions which are stabilized for storage and administration to humans are described in U.S. Pat. No. 5,945,098, incorporated fully herein by reference. Other agents, such as human serum albumin (HSA), may be added to the therapeutic or imaging composition to stabilize the antibody conjugates.

The compositions of the invention may be administered using any medically appropriate procedure, e.g., intravascular (intravenous, intraarterial, intracapillary) administration, injection into the cerebrospinal fluid, intracavity, subcutaneously, or direct injection in the tumor. For the imaging compositions of the invention, administration via intravascular injection is preferred for pre-operative visualization of the tumor.

The effective amount of the therapeutic antibody-conjugate composition or of the imaging antibody-conjugate compositions to be given to a particular patient will depend on a variety of factors, several of which will be different from patient to patient. A competent clinician will be able to determine an effective amount of a therapeutic antibody-conjugate composition to administer to a patient to retard the growth and promote the death of tumor cells, or an effective amount of an imaging composition to administer to a patient to facilitate the visualization of a tumor. Dosage of the antibody-conjugate will depend on the treatment of the tumor, route of administration, the nature of the therapeutics, sensitivity of the tumor to the therapeutics, etc. Utilizing $LD_{50}$ animal data, and other information available for the conjugated cytotoxic or imaging moiety, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Imaging moieties are typically less toxic than cytotoxic moieties and may be administered in higher doses in some embodiments. Utilizing ordinary skill, the competent clinician will be able to optimize the dosage of a particular therapeutic or imaging composition in the course of routine clinical trials.

Typically the dosage will be 0.001 to 100 milligrams of conjugate per kilogram subject body weight. Doses in the range of 0.01 to 1 mg per kilogram of patient body weight may be utilized for a radionuclide therapeutic composition which is administered intrathecally. Relatively large doses, in the range of 0.1 to 10 mg per kilogram of patient body weight, may used for imaging conjugates with a relatively non-toxic imaging moiety. The amount utilized will depend on the sensitivity of the imaging method, and the relative toxicity of the imaging moiety. In a therapeutic example, where the therapeutic composition comprises a $^{131}$I cytotoxic moiety, the dosage to the patient will typically start at a lower range of 10 mCi, and go up to 100, 300 or even 500 mCi. Stated otherwise, where the therapeutic agent is $^{131}$I, the dosage to the patient will typically be from 5,000 Rads to 100,000 Rads (preferably at least 13,000 Rads, or even at least 50,000 Rads). Doses for other radionuclides are typically selected so that the tumoricidal dose will be equivalent to the foregoing range for $^{131}$I. Similarly, chemotoxic or toxin protein doses may be scaled accordingly.

The antibody conjugate can be administered to the subject in a series of more than one administration. For therapeutic compositions, regular periodic administration (e.g., every 2-3 days) will sometimes be required, or may be desirable to reduce toxicity. For therapeutic compositions which will be utilized in repeated-dose regimens, antibody moieties which do not provoke HAMA or other immune responses are preferred. The imaging antibody conjugate compositions may be administered at an appropriate time before the visualization technique. For example, administration within an hour before direct visual inspection may be appropriate, or administration within twelve hours before an MRI scan may be appropriate. Care should be taken, however, to not allow too much time to pass between administration and visualization, as the imaging compound may eventually be cleared from the patient's system.

Methods for Transplantation

In other therapeutic methods, hematopoietic cells, including without limitation HSC, hematopoietic progenitors, normal bone marrow, or mobilized peripheral blood for patients with a clinical indication for hematopoietic transplantation, are protected from phagocytosis in circulation by providing a host animal with an agent that blocks the interaction between CRT and LRP, e.g. an antibody selective for CRT, an antibody selective for LRP, soluble CRT or LRP, a CRT blocking peptide, and the like, is administered, which blocks the pro-phagocytic signal and decreases the clearance of the hematopoietic cells from circulation. In some embodiments of the invention, the agent, e.g. peptide, soluble CRT, etc. is provided as a fusion protein, for example fused to an Fc fragment, e.g., IgG1 Fc, IgG2 Fc, Ig A Fc etc.

The subject invention provide for methods for transplanting hematopoietic cells into a mammalian recipient. A need for transplantation may be caused by genetic or environmental conditions, e.g. chemotherapy, exposure to radiation, etc. The cells for transplantation may be mixtures of cells, e.g. buffy coat lymphocytes from a donor, or may be partially or substantially pure. The cells may be autologous cells, particularly if removed prior to cytoreductive or other therapy, or allogeneic cells, and may be used for hematopoietic stem or progenitor cell isolation and subsequent transplantation.

The cells may be combined with calreticulin blocking agent, including a blocking peptide, blocking oligosaccharide, blocking antibody, etc. prior to transplantation or transfusion. For example, the cells may be combined with the blocking agent at a concentration of from about 10 μg/ml, about 100 μg/ml, about 1 mg/ml, about 10 mg/ml, etc., at a temperature of from about 4°, about 10°, about 25° about 37°, for a period of time sufficient to coat the cells, where in some embodiments the cells are maintained on ice. In other embodiments the cells are contacted with the CTR blocking agent immediately prior to introduction into the recipient, where the concentrations are as described above.

The composition comprising hematopoietic cells and a CTR blocking agent is administered in any physiologically acceptable medium, normally intravascularly, although they may also be introduced into bone or other convenient site, where the cells may find an appropriate site for regeneration and differentiation. Usually, at least $1\times10^5$ cells will be administered, preferably $1\times10^6$ or more. The composition may be introduced by injection, catheter, or the like.

Example 1

Therapeutic and Diagnostic Methods for Manipulating Phagocytosis Through Calreticulin and Low Density Lipoprotein-Related Receptor Cell Surface Calreticulin is Expressed on Cancer, but not Most Normal, Stem and Progenitor Cells.

Figure 1B:
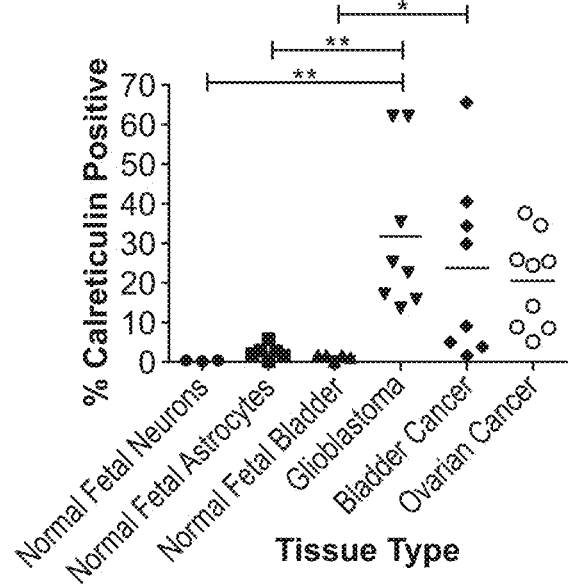

Cell surface calreticulin expression was determined on a variety of primary human cancer cells and their normal cell counterparts by flow cytometry. In hematologic malignancies, cell surface calreticulin was expressed on a greater percentage of bulk cells in AML (average=23.9%), acute lymphocytic leukemia (ALL, 17.6%), chronic phase chronic myeloid leukemia (CML, 47.6%), and NHL (18.3%) when compared to normal bone marrow (2.6%) and normal peripheral blood cells (2.6%) (FIG. 1A). In solid tumors, cell surface calreticulin was also expressed on a greater percentage of bulk cells in ovarian cancer (average=20.5%), glioblastoma (31.7%), and bladder cancer (23.7%) when compared to normal fetal neurons (0.3%), astrocytes, (2.5%) and normal fetal bladder cells (1.41%) (FIG. 1B). In this analysis, annexin V-positive cells were excluded, indicating that calreticulin-positive cancer cells were not a part of the apoptotic subset. In addition, calreticulin positive-cancer cells (from AML and bladder cancer patients) formed tumors when engrafted into immunodeficient mice similarly to CRT-negative cancer cells, indicating that CRT-positive cancer cells were functionally viable and possess tumorigenic potential in vivo (FIG. 5).

Figure 6A:
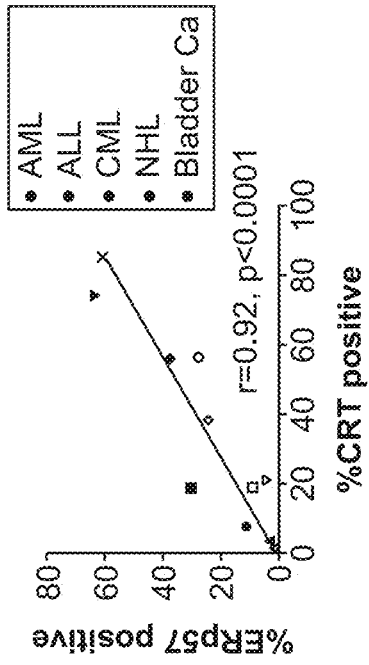
FIGS. 6A-6C. Cell surface CRT correlates with ERp57 expression on tumor cells.
Figure 6B:
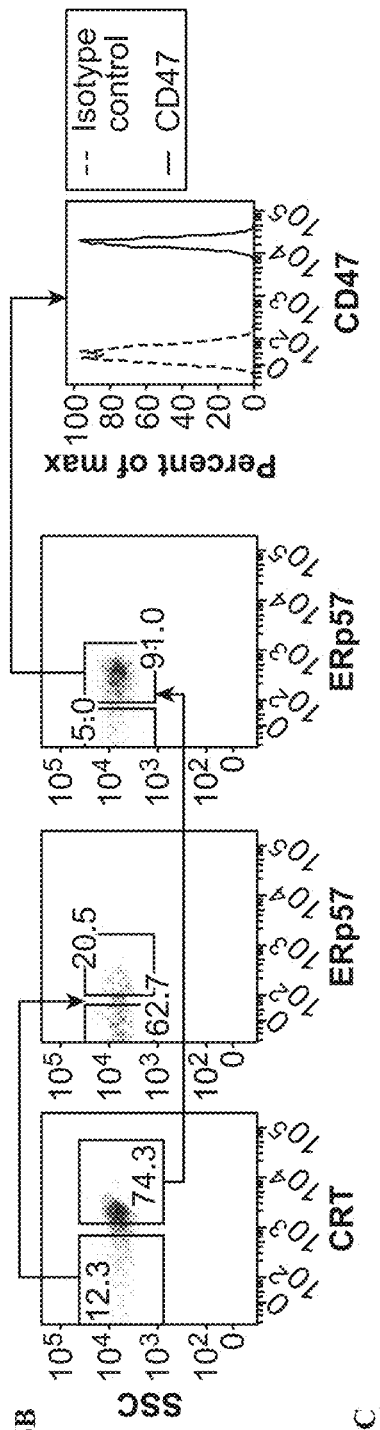
Figure 6C:
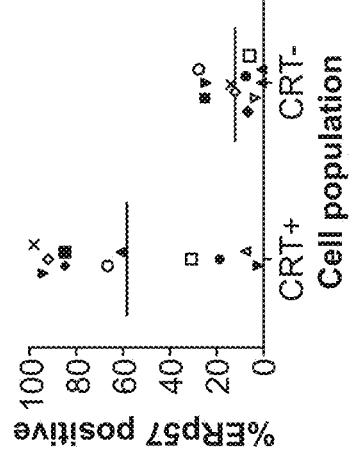

Previous studies have identified that the endoplasmic reticulum (ER) protein ERp57 co-translocates with CRT to the cell surface and is required for CRT cell surface exposure under conditions of apoptosis. Accordingly, we assessed the relationship between cell surface CRT and ERp57 expression on tumor cells. On non-apoptotic (annexin V negative) tumor cells, cell surface ERp57 expression was associated with cell surface CRT expression (FIG. 6A). Furthermore, across several different tumor types (including primary human tumor samples and cancer cell lines), ERp57 was expressed on a higher percentage of CRT+ cells compared to CRT− counterparts (FIG. 6B,C).

Figure 1C:
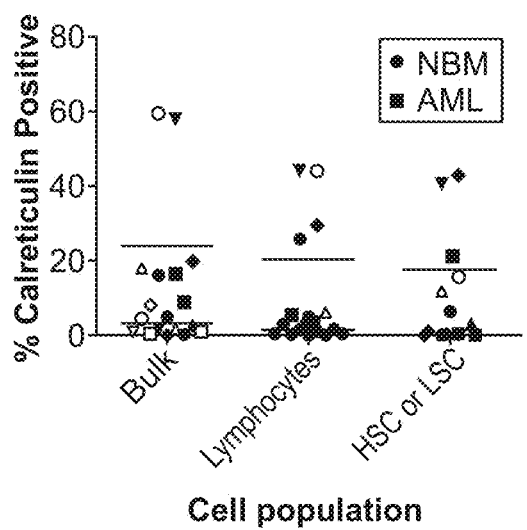
Figure 1D:
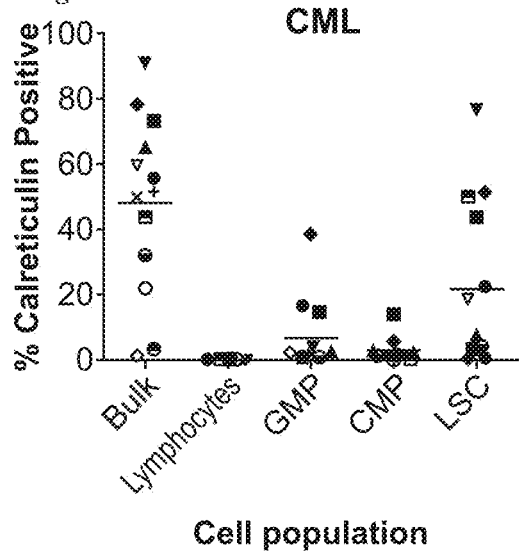
Figure 1E:
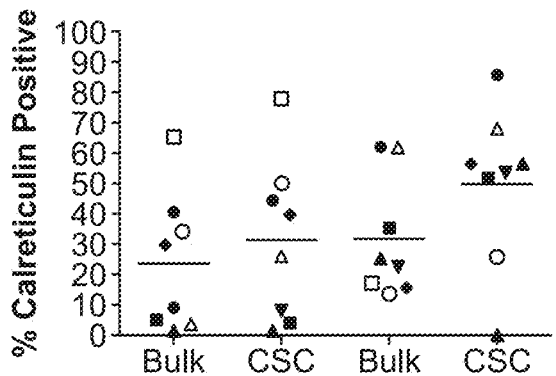
Figure 10A:
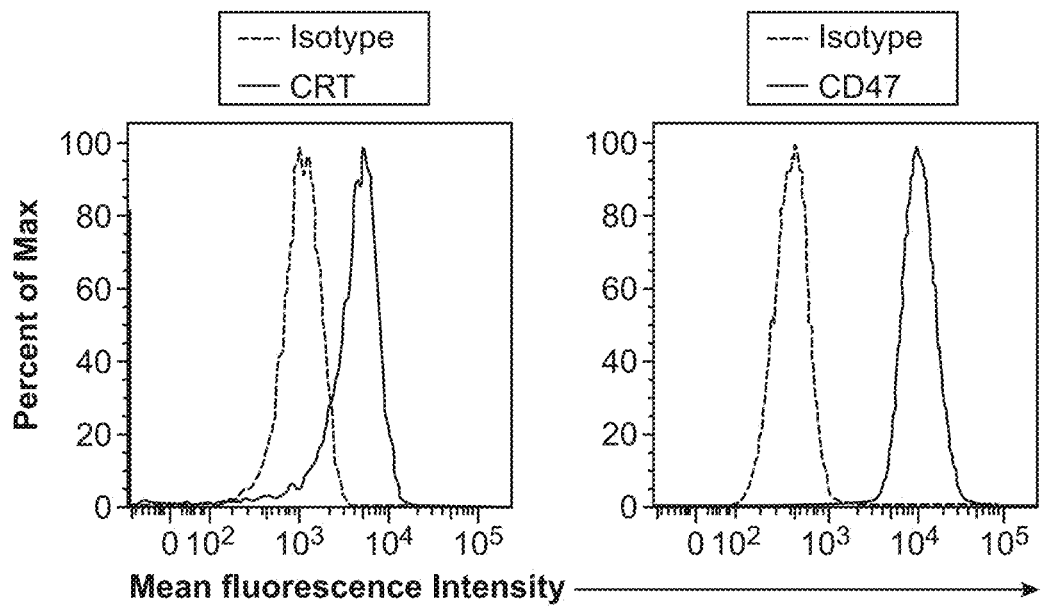
FIGS. 10A-10B. Abrogation of anti-CD47 antibody-mediated phagocytosis is dose dependent on calreticulin blockade.
Figure 10B:
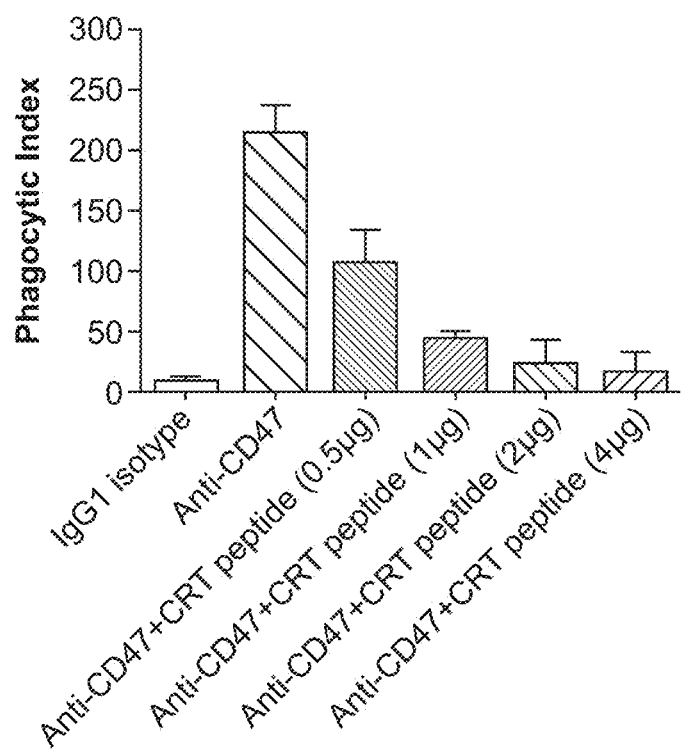
Figure 12:
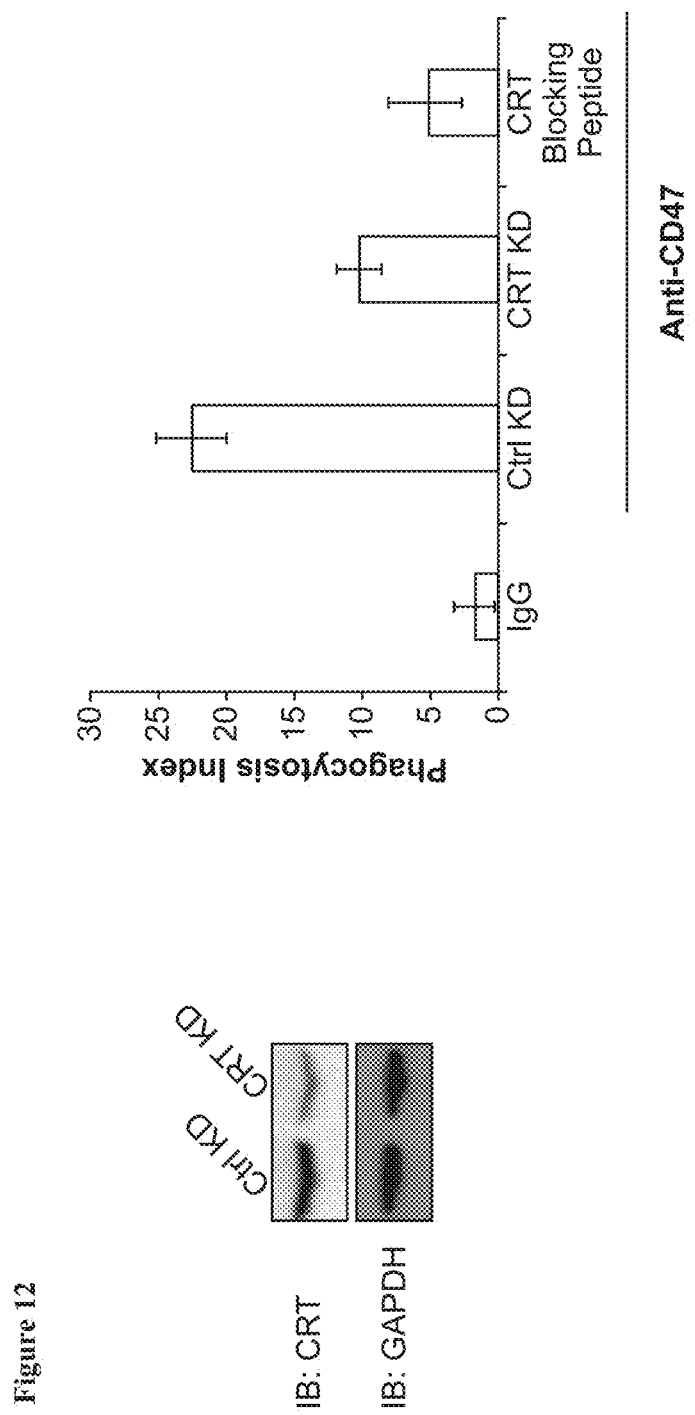
FIG. 12. CRT was knocked down in HL60 human leukemia cells by infection with lenti viruses expressing control shRNA (control KD) or shRNA targeting CRT (CRT KD). (left Panel) Knockdown (KD) efficiency was evaluated by western blot (IB) with anti-CRT antibody, and GAPDH was used as a loading control. (Right Panel) HL60 cells treated with control KD, CRT KD or CRT blocking peptide were treated with anti-CD47 antibody (B6H12) or IgG control, and incubated with J774 macrophages for phagocytosis as described above. The phagocytic index of the CRT KD cells was about half of the control KD cells and the CRT peptide blocked ~75% of the phagocytosis observed when treated with anti CD47 antibody indicating that reducing or blocking the prophagocytic signal CRT allows phagocytosis to proceed in the presence of antiCD47 antibody.
Figure 13:
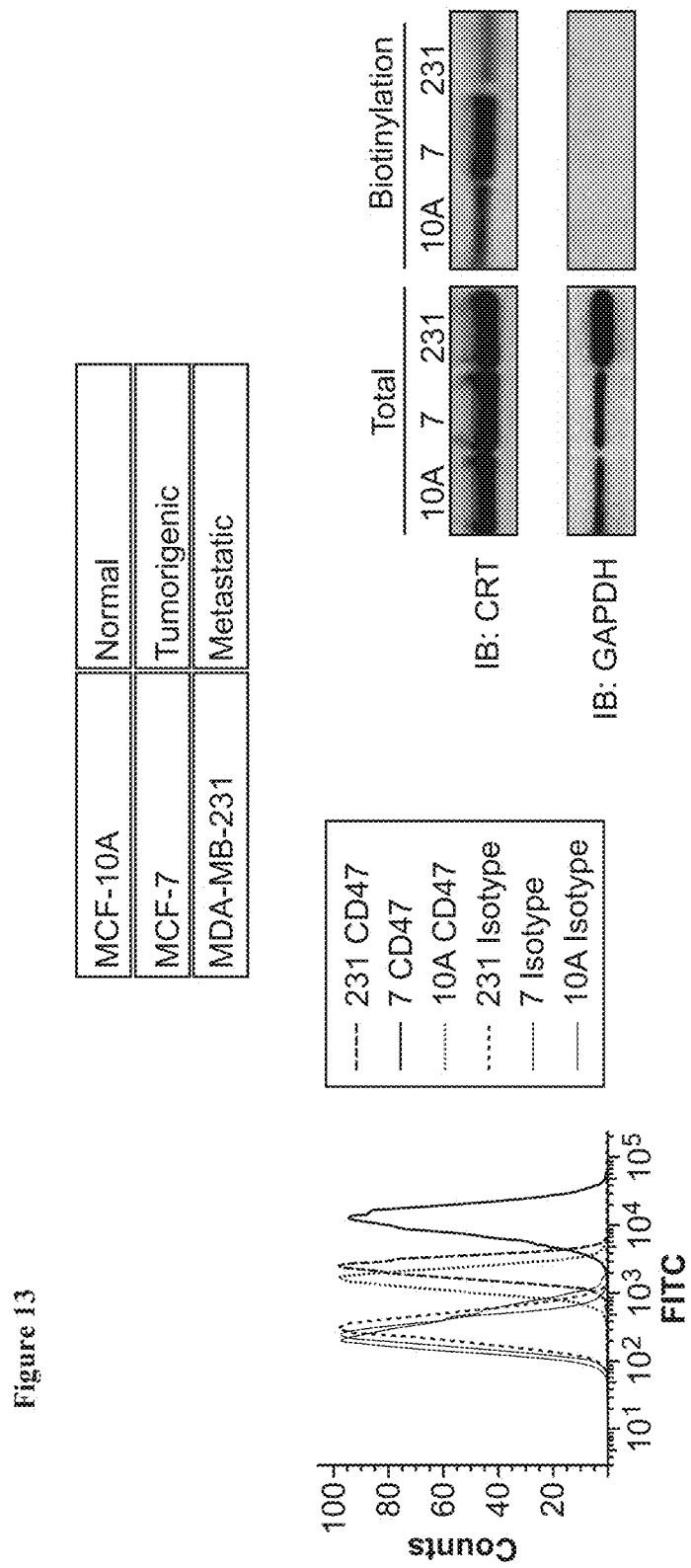
FIG. 13. CRT and CD47 expression were examined in MCF-10A (10A, normal human breast epithelial cell line), MCF-7 (7, tumorigenic human breast cancer cell line) and MDA-MB-231 (231, metastatic human breast cancer cell line). (Lower left) Histograms of CD47 expression as determined by flow cytometry on each of the above cell lines with FITC-conjugated anti-CD47 antibody and isotype matched control antibody indicating that tumorigenic MCF-7 cells express high levels of CD47. The metastatic (231) breast cancer cell line expressed lower level of CD47, but slightly higher than the normal breast cell line (10A). (Lower Right) Surface biotinylation to detect surface CRT expression, Sulfo-NHS-SS-Biotin was used to label cell surface proteins and cell lysate was then incubated with neutravidin beads to collect biotin labeled proteins. Surface biotin-labeled CRT was detected by Western analysis with anti-CRT antibody and cytosolic protein GAPDH was used as a negative control. Consistent with the flow cytometry data, higher levels of surface CRT were observed in tumorigenic MCF-7 cells than in the normal (10A) or metastatic (231) breast cancer lines.
Figure 14A:
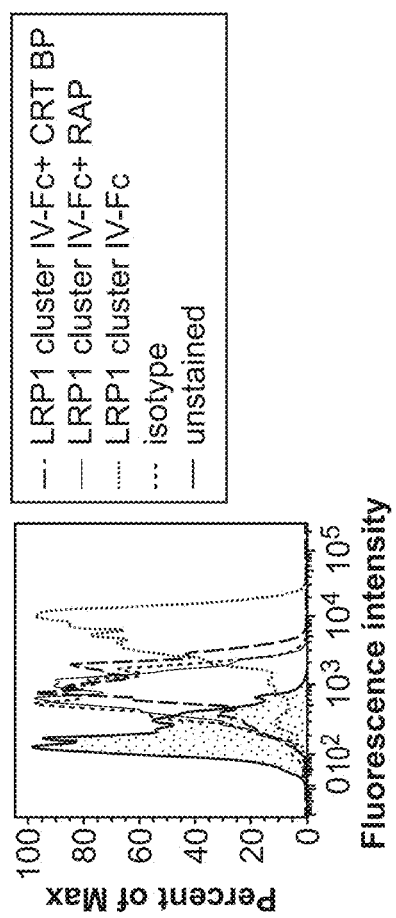
FIGS. 14A-14B. Calreticulin on the cell surface of cells undergoing apoptosis bind to LRP1 protein.
Figure 14B:
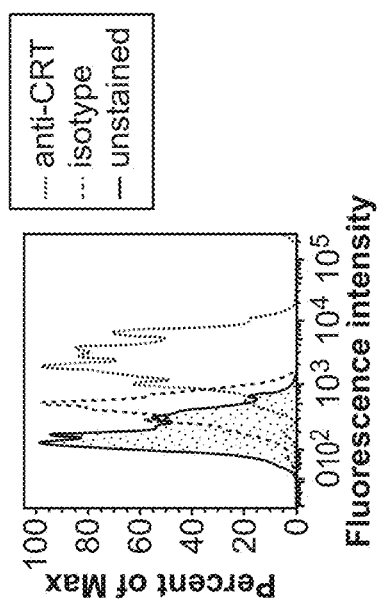
Figure 15A:
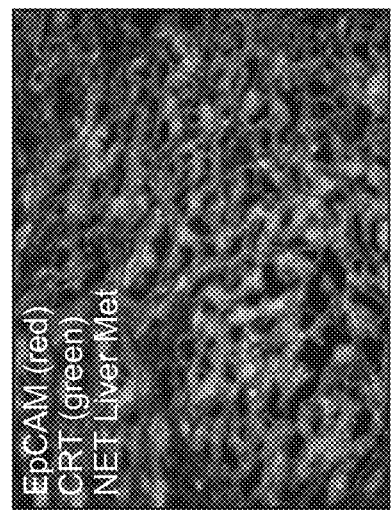
FIGS. 15A-15B. Calreticulin is expressed on the cell surface of viable, non-apoptotic cells tumor cells. Pancreatic cancer cell line and primary tumors express calreticulin. Paca-2 cells were fixed and stained with anti-calreticulin (CRT) and secondary antibody (FIG. 15A). Arrows show expression of calreticulin on the cell surface. A human primary neuroendocrine tumor sample was sectioned, fixed and stained with anti-CRT, and cell surface marker EpCAM, and nuclear stain Dapi (FIG. 15B).
Figure 15B:
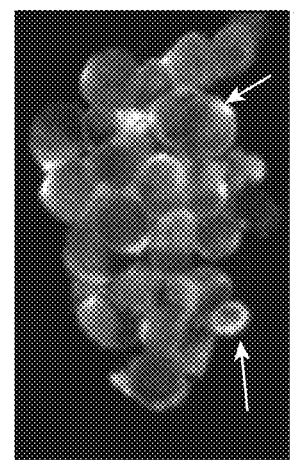

Given that primary human tumors are heterogeneous and contain a subpopulation of tumor-initiating cells, we next investigated whether cell surface calreticulin was present on the cancer stem cell (CSC) population of each tumor type in which the immunophenotype of functional CSC is known. In AML and chronic phase CML, cell surface calreticulin was expressed on CD34+CD38-CD90-Lin− AML (19, 20) and CD34+CD38-CD90+ chronic phase CML leukemia stem cells (LSC), as well as downstream progenitor populations, while normal bone marrow hematopoietic stem and progenitor populations expressed minimal cell surface calreticulin (FIG. 1C,D). For AML, similar levels of cell surface calreticulin expression were observed for LSC compared to other cellular subsets (FIG. 10). In contrast, CML LSC expressed higher levels of cell surface calreticulin compared to downstream CMP and GMP populations (FIG. 1D). Cell surface calreticulin was also expressed on CSC of solid tumors including CD44+Lin− bladder CSC and CD133+Lin− glioblastoma CSC (22, 23) (FIG. 1E).

Figure 2A:
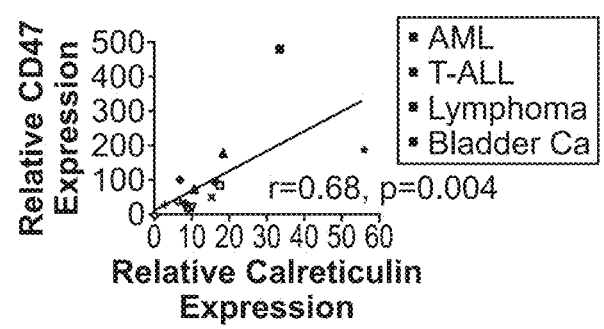
FIGS. 2A-2E. Increased CD47 Expression on Cancer Cells Protects Them from Calreticulin-Mediated Phagocytosis (FIG. 2A) Correlation between cell surface calreticulin and CD47 expression was determined for human cancer cell lines (top left) and primary human normal and cancer samples (top right, bottom panels). Expression was calculated as mean fluorescence intensity normalized over isotype control and for cell size. Pearson correlation (r) and p-value is shown for each correlation. Top left panel: blue solid circle=HL60, blue open circle=Kasumi1, blue open inverted triangle=MOLM13, blue open diamond=KG-1, red triangle=Jurkat, red solid square=CCRF-CEM, red open square=CCRF-HSB2, red diamond=MOLT4, black star=Raji, black open diamond=SUDHL6, black open triangle=Daudi, black x=U937, green plus=639V, green open diamond=HT1197, green inverted triangle=UMUC3.
Figure 2A:
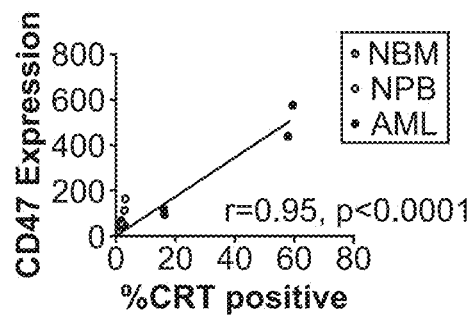
Figure 2A:
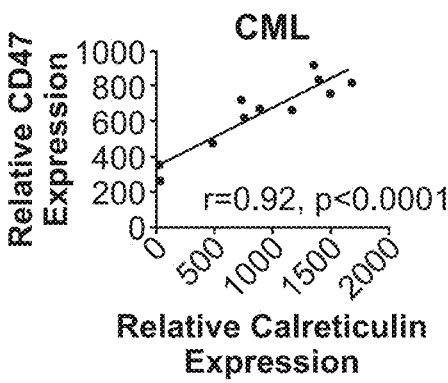
Figure 2A:
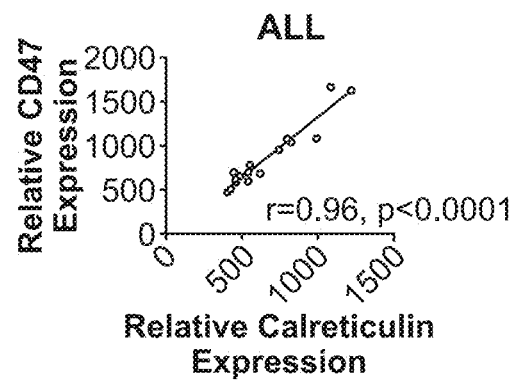

We next determined whether there was a correlation between calreticulin (CRT) and CD47 expression in human tissues, postulating that a balance between pro- (CRT) and anti- (CD47) phagocytic signals may be maintained as a homeostatic mechanism. CRT and CD47 cell surface expression were profiled in a variety of human cancer cell lines, primary cancers, and normal cells. CD47 expression correlated with CRT expression in a variety of hematologic and solid tumor cell lines as well as in primary human AML, CML, and ALL patient samples (FIG. 2A). Notably, normal cells expressed minimal levels of both CRT and CD47 (FIG. 2A, top panels). In normal human bone marrow and fetal bladder, those cells that were CRT positive expressed higher levels of CD47 compared to CRT negative cellular counterparts (FIG. 7). Thus, in both normal and cancer cells, there is a strong positive correlation between CRT and CD47 expression.

Increased CD47 on Cancer Cells Protects them from Calreticulin-Mediated Phagocytosis.

Figure 2B:
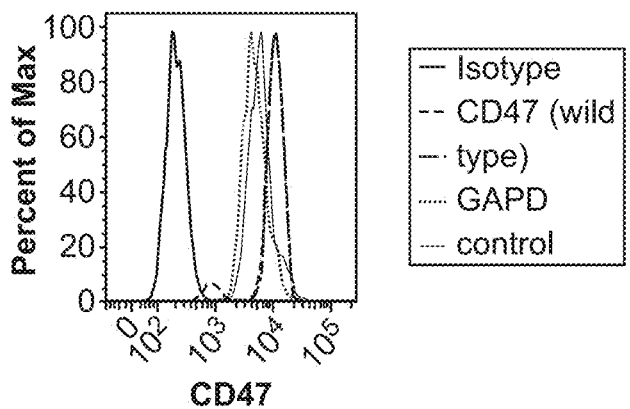
Figure 2C:
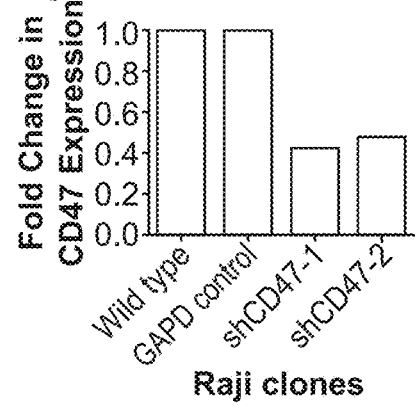
Figure 2D:
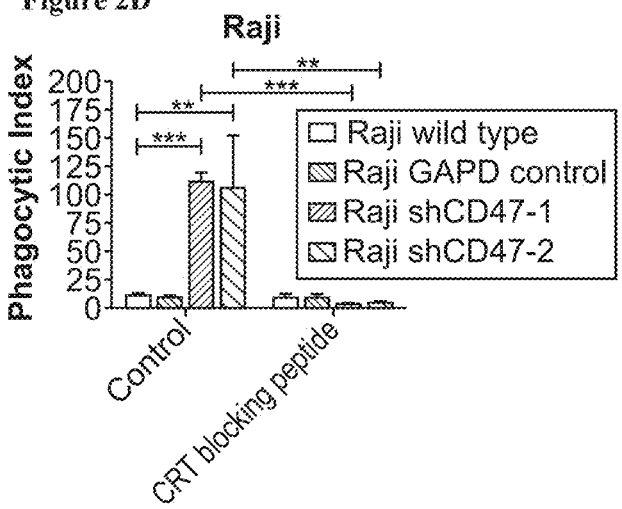
Figure 2E:
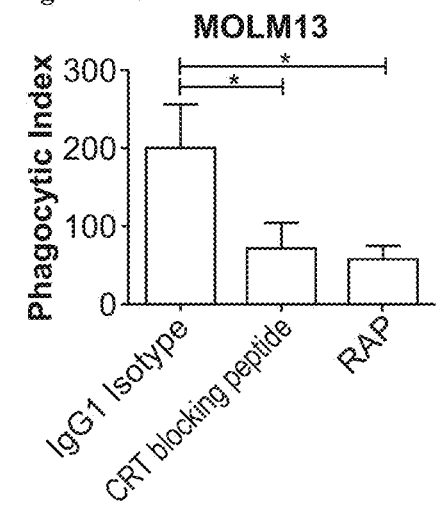
Figure 8:
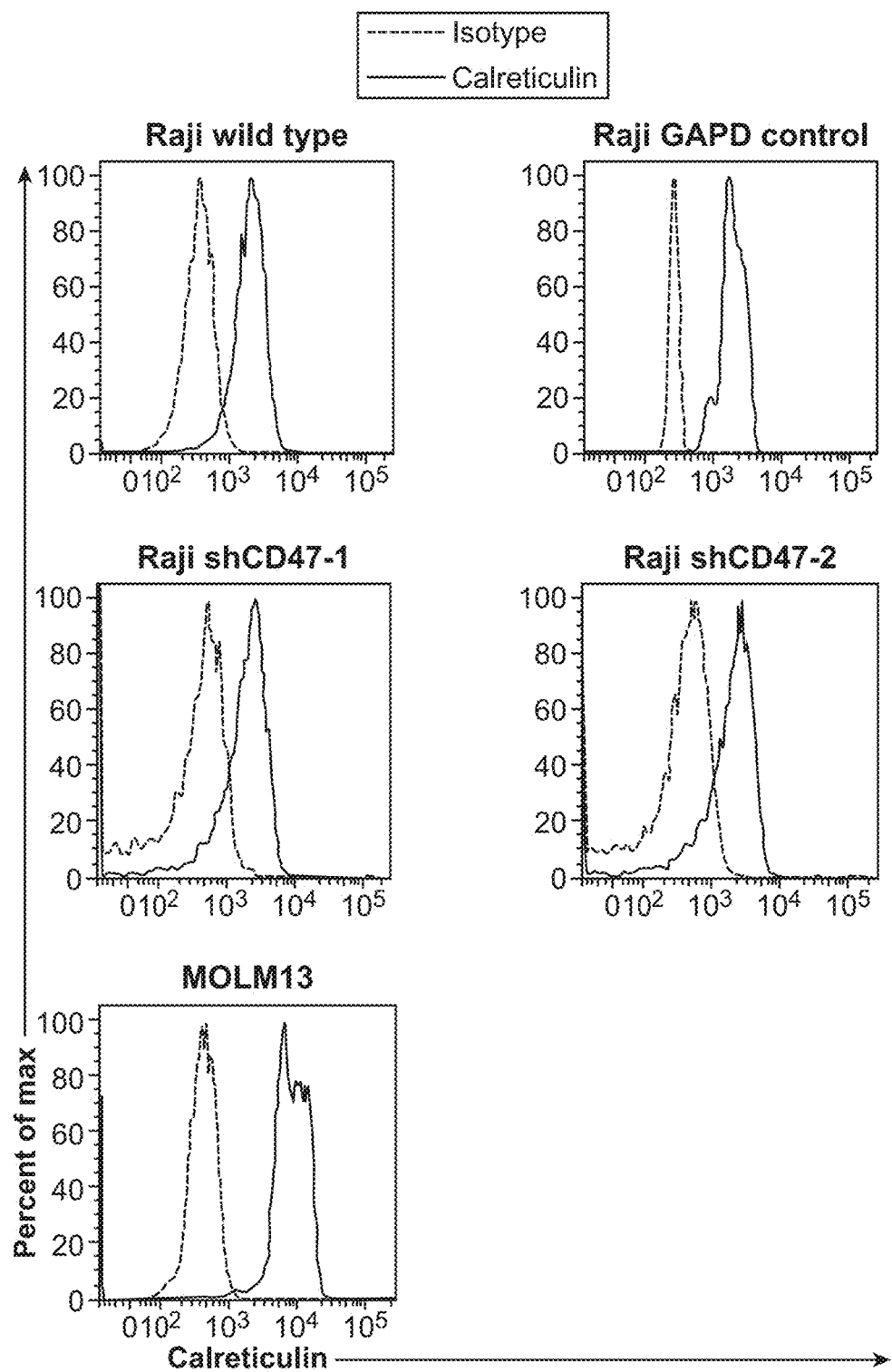
FIG. 8 Calreticulin expression is unaffected by CD47 shRNA knockdown in Raji cells. Raji cells were transduced with lentiviral constructs encoding shRNA directed against CD47 (Raji shCD47-1, shCD47-2) or a GAPD control (Raji GAPD). Cell surface calreticulin expression was determined by flow cytometry and demonstrated no difference on wild type, untransduced Raji cells compared to Raji cells transduced with either GAPD control, shCD47-1, or shCD47-2 lentivirus. Cell surface calreticulin expression for MOLM 13 cells is also shown.

We observed increased cell surface calreticulin and CD47 on human cancer cells leading us to hypothesize that increased CD47 protects these cells from calreticulin-mediated phagocytosis. To investigate this hypothesis, we performed in vitro phagocytosis assays on two different CRT-expressing cancer cell lines: one expressing high CD47 levels (Raji) and one deficient in CD47 expression (MOLM13). First, Raji cells, a Burkitt's NHL cell line that expresses high levels of CD47 and calreticulin (FIG. 2B and FIG. 8), were incubated with human macrophages under conditions where CD47 expression was knocked down to various levels by lentiviral transduction of shRNAs (FIG. 2B,C). Cell surface calreticulin expression was unaffected by shRNA-mediated CD47 knockdown (FIG. 8). Upon incubation with human macrophages, Raji cells with approximately 2 fold knockdown of CD47 expression (shCD47-1 and shCD47-2) were more robustly phagocytosed by human macrophages than were wild type and GAPD control transduced Raji cells which were the minimally phagocytosed (FIG. 2D). Phagocytosis of shCD47-1 and shCD47-2 Raji cells was dependent on the calreticulin-LRP interaction as the observed phagocytosis was completely abrogated in the presence of a CRT blocking peptide (FIG. 2D). In the second experiment, MOLM13 cells, a human AML cell line that is deficient in CD47 expression but expresses calreticulin (FIG. 8), were incubated with human macrophages. As expected, MOLM13 cells were robustly phagocytosed at baseline, while phagocytosis was significantly reduced when the CRT-LRP interaction was blocked (FIG. 2E). These findings demonstrate that overexpression of CD47 in cancers counterbalances calreticulin-mediated phagocytosis.

Calreticulin is the dominant pro-phagocytic signal on several human cancers and is required for anti-CD47 antibody-mediated phagocytosis. In prior studies, we demonstrated that in several human cancers overexpression of CD47 contributes to evasion of macrophage phagocytosis, and furthermore that monoclonal antibody-mediated blockade of CD47 can enable phagocytosis and elimination of tumors in vitro and in mouse xenografts. However, we also showed that normal hematopoietic progenitor cells, which express CD47, were not phagocytosed when coated with anti-CD47 antibody. Additionally, administration of a blocking anti-mouse CD47 antibody to wild type mice caused minimal tissue toxicity. The lack of antibody toxicity is not likely exclusively due to overexpression of CD47 on cancer cells compared to normal counterparts given that both normal and cancer cells are coated with anti-CD47 antibody at therapeutic doses. Instead, it is likely a result of the fact that, in order for target cells to be phagocytosed upon blockade of an anti-phagocytic signal (CD47), the cells must also display a potent pro-phagocytic signal, which is absent on normal cells.

Figure 9A:
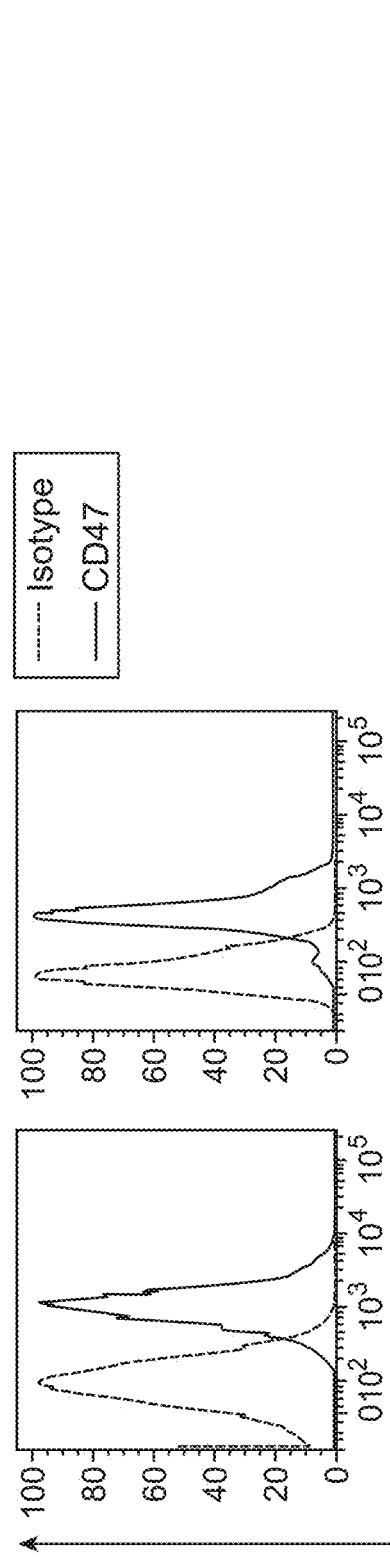
FIGS. 9A-9B. CD47 is expressed on normal human cells.
Figure 9B:
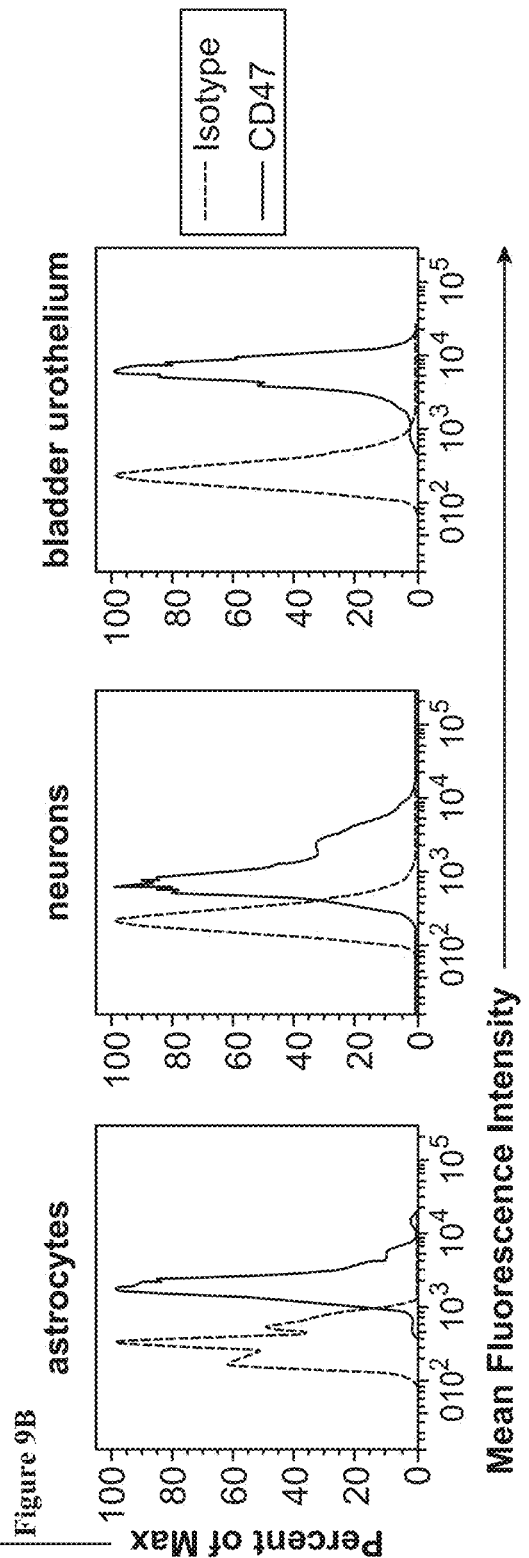

Given the known role of CRT as a pro-phagocytic signal, its correlation with CD47 expression (FIG. 2A), and its ability to be counteracted by CD47 (FIG. 2), we investigated whether the expression of cell surface CRT on cancer but not normal cells could explain the selective targeting of tumor cells by a blocking anti-CD47 antibody. In vitro phagocytosis assays were performed by incubating primary human normal cells or cancer cells with human macrophages in the presence of anti-CD47 antibody. CD47 was expressed on all normal and cancer cells profiled (FIG. 2A and FIG. 7, 9), but expression of calreticulin was primarily restricted to tumor cells (FIG. 1A,B). No phagocytosis of cells from a variety of normal human tissue types was observed with anti-CD47 antibody (FIG. 3B), while primary cancer cells from a variety of tumor types were robustly phagocytosed (FIG.

Figure 3A:
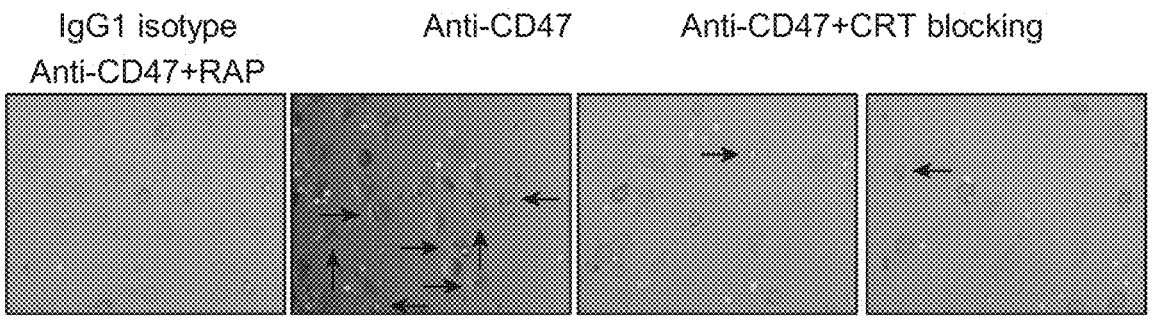
FIGS. 3A-3E. Cell Surface Calreticulin is the Dominant Pro-Phagocytic Signal on Several Human Cancers and is Required for Anti-CD47 Antibody-Mediated Phagocytosis (FIG. 3A) Primary human AML cells were fluorescently-labeled with CFSE and incubated with human macrophages in the presence of the indicated antibodies/peptides for 2 hours, after which phagocytosis was analyzed by fluorescence microscopy. Arrows indicate phagocytosis.
Figure 3B:
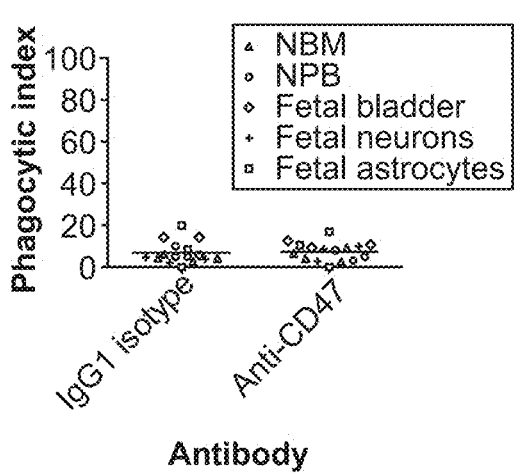
Figure 3C:
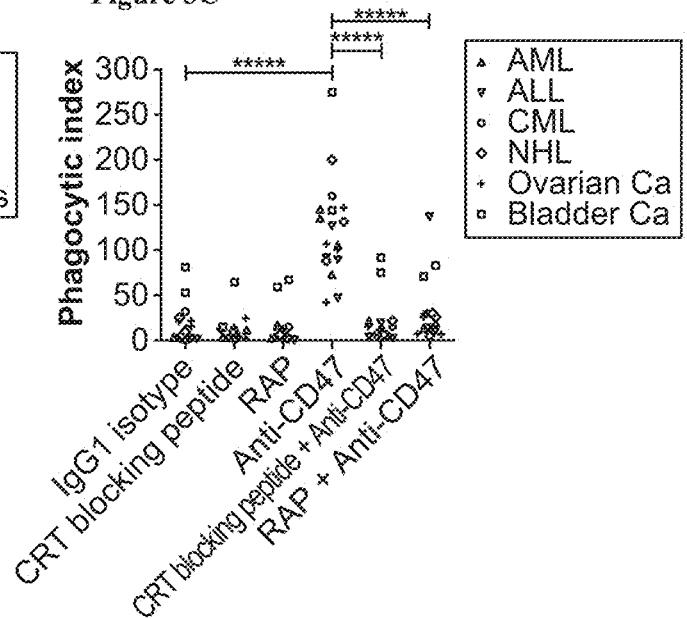

3A,C). Significantly, anti-CD47 antibody-mediated phagocytosis of cancer cells was completely abrogated in most cases when cells were simultaneously incubated with peptides that inhibit the CRT-LRP interaction, including a calreticulin blocking peptide and receptor-associated protein (RAP), an inhibitor of LRP (see Gardai et al. *Cell.* 123, 321-334 (2005), herein specifically incorporated by reference). (FIG. 3C).

Increasing concentrations of a calreticulin blocking peptide lead to a dose-dependent reduction in anti-CD47 antibody mediated phagocytosis (FIG. 10). Notably, additional blockade of other pro-phagocytic signals was not required to abolish anti-CD47 antibody-mediated phagocytosis, as cells incubated with anti-CD47 antibody under CRT-LRP blockade were phagocytosed at levels similar to baseline controls (FIG. 3C). However, two bladder cancer samples exhibited higher baseline levels of phagocytosis with IgG1 isotype control compared to other cancer cell types which may be due to expression of other pro-phagocytic signals on these specific cells. Nevertheless, blockade of CRT or LRP in the presence of anti-CD47 antibody abrogated phagocytosis of these bladder cancer cells to levels similar to IgG1 isotype controls. Blockade of the calreticulin-LRP interaction alone by CRT blocking peptide or LRP had no effect on phagocytosis when compared to IgG control (FIG. 3C).

Figure 3D:
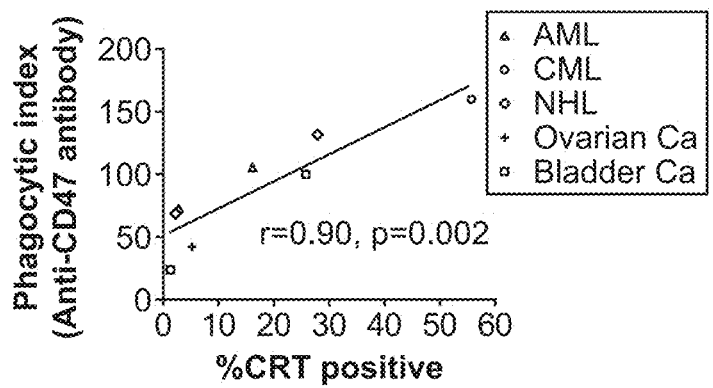
Figure 3E:
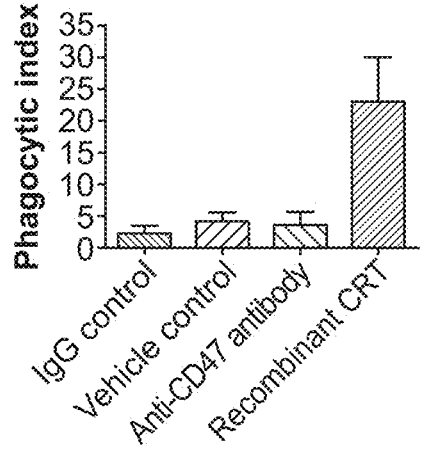

Next, the relationship between the level of tumor cell surface CRT expression and level of phagocytosis by anti-CD47 antibody was investigated. Cell surface CRT expression on tumor cells positively correlated with the degree of anti-CD47 antibody mediated phagocytosis, regardless of tumor cell type (FIG. 3D). Finally, given that normal cells express minimal levels of cell surface CRT, we investigated whether the addition of CRT to the surface of these cells could enable phagocytosis. An in vitro phagocytosis assay was performed on NBM cells incubated with exogenous recombinant calreticulin protein, previously demonstrated to adsorb onto the cellular surface and directly bind LRP. In contrast to vehicle control, incubation with exogenous CRT enabled phagocytosis of NBM cells while anti-CD47 antibody did not (FIG. 3E). Collectively, these results demonstrate that anti-CD47 antibody-mediated phagocytosis requires the presence of cell surface calreticulin.

Increased Calreticulin Expression Confers a Worse Clinical Prognosis in Multiple Human Malignancies.

Figure 4A:
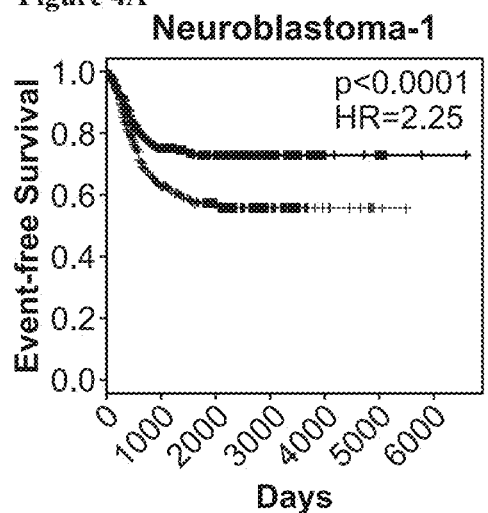
FIGS. 4A-4F. Increased calreticulin expression confers a worse clinical prognosis in multiple human malignancies. Stratification of clinical outcomes based on the level of expression of calreticulin mRNA is shown in previously described cohorts of patients with diverse malignancies including neuroblastoma (FIG. 4A,4B), superficial or invasive bladder cancer (FIG. 4C,4D), and mantle cell lymphoma (FIG. 4E,4F). Patients were divided into calreticulin high and low expression groups based on median calreticulin expression with Kaplan-Meier analyses of patient outcome shown. Hazard ratios (HR) and log-rank p values are shown for the relationship of outcomes to continuous expression of calreticulin using a univariate Cox regression model. HR, 95% confidence intervals, and log-rank p values for calreticulin expression as a dichotomous variable are shown in table 1. Description of clinical datasets is shown in table 1.
Figure 4B:
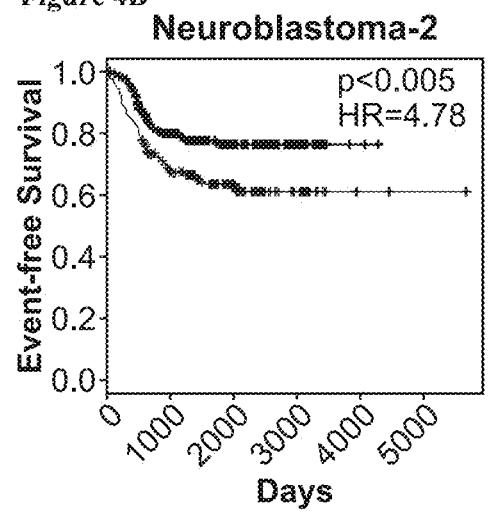
Figure 4C:
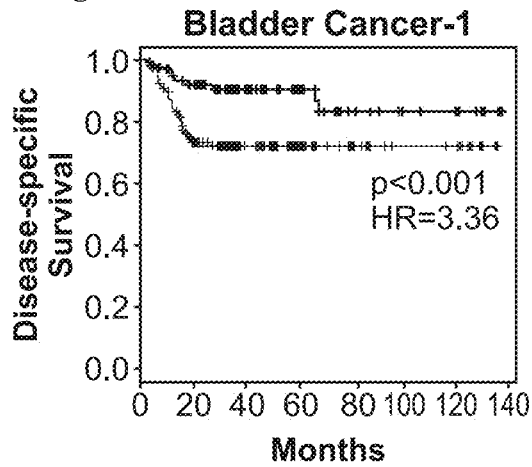
Figure 4D:
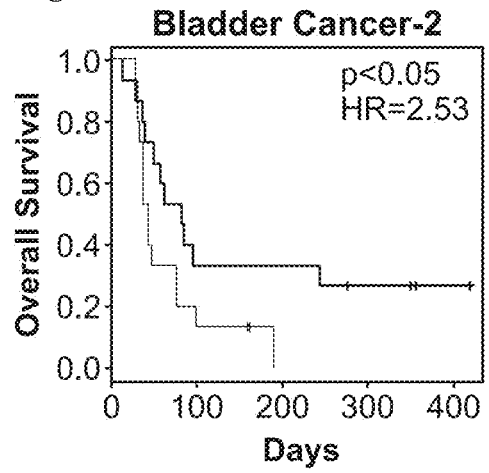
Figure 4E:
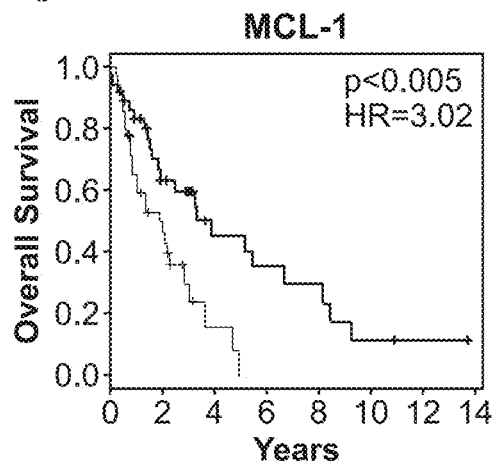
Figure 4F:
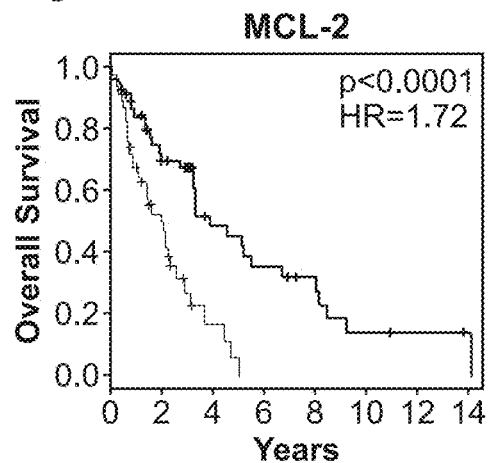
Figure 5A:
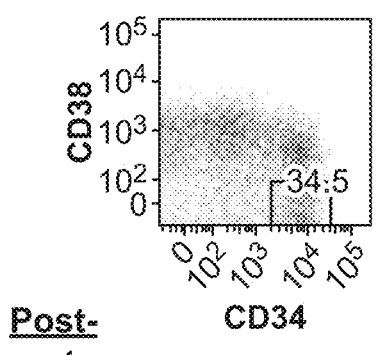
FIGS. 5A-5E. Live calreticulin positive cancer cells form tumors in vivo (FIG. 5A) CRT− and CRT+ LSC from human AML patient samples were sorted to 100% purity by FACS.
Figure 5A:
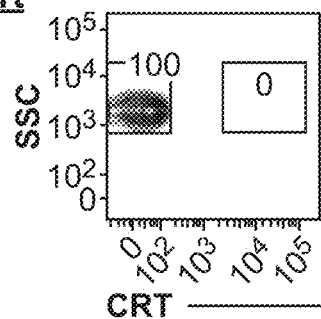
Figure 5B:
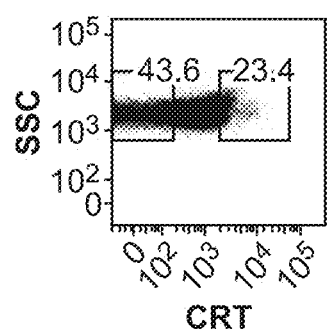
Figure 5B:
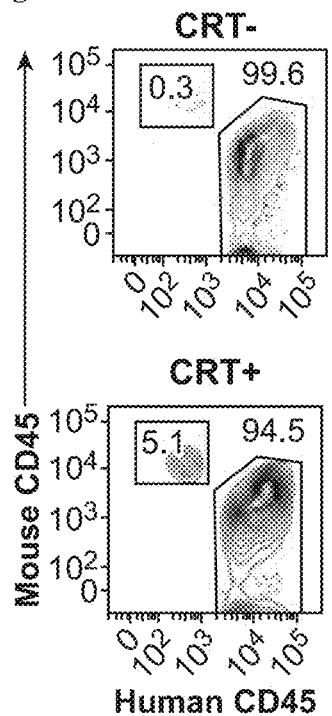
Figure 5C:
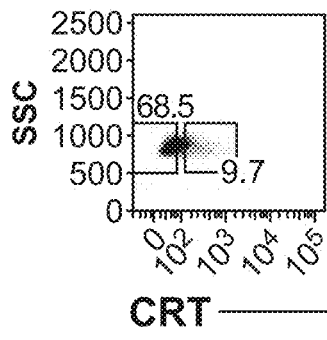
Figure 5C:
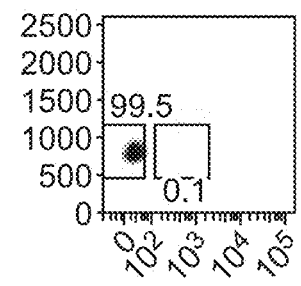
Figure 5C:
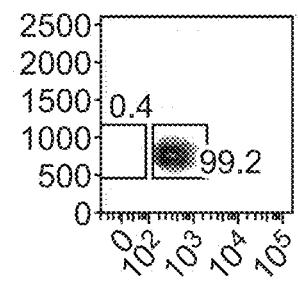
Figure 5D:
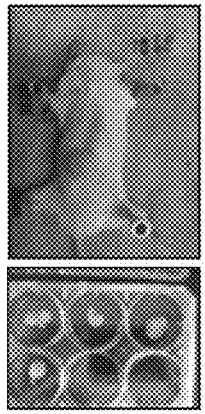
Figure 5D:
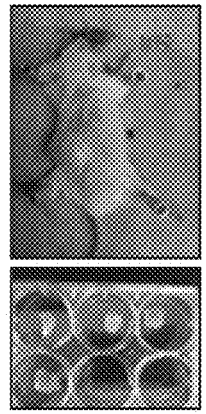
Figure 5E:
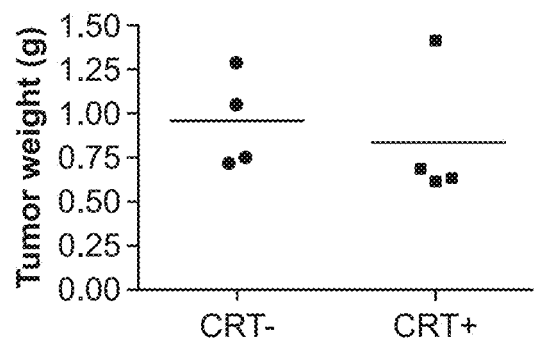

Lastly, we sought to investigate the clinical relevance of these findings by investigating the association between CRT expression and clinical outcomes. We analyzed calreticulin mRNA levels in patients with human malignancies of distinct tumor types and investigated their correlation with tumor progression and clinical outcome. Utilizing previously published gene profiling datasets with associated clinical outcome data, we determined calreticulin expression in both hematologic and solid tumor malignancies, including non-Hodgkin lymphoma (mantle cell lymphoma (MCL)), superficial and invasive bladder cancer, and neuroblastoma. Patients were stratified into calreticulin high and low-expressing cohorts relative to the median value and analyzed for clinical outcomes. For each tumor type, correlations between calreticulin expression and event-free, disease-specific, or overall survival were measured in two independent datasets to test and validate significant associations. Regardless of tumor type, higher calreticulin expression predicted a worse clinical outcome in all malignancies analyzed: neuroblastoma (FIG. 4A,B), bladder cancer (FIG. 4C,D), and NHL (MCL, FIG. 4E,F). These associations were significant when calreticulin expression was considered either as a dichotomous variable (relative to the median) or as a continuous variable (table 1). The prognostic power of CRT was independent from type of therapy as patients with the various tumors received disparate treatments including observation, surgery, or chemotherapy (table 1). Additionally, the prognostic power of CRT was preserved in both early and late stage tumors as increased calreticulin levels correlated with worse survival in both superficial and invasive bladder cancer (FIG. 4C.D, table 1). Thus, calreticulin expression is associated with tumor progression and worse clinical outcome across several tumor types.

TABLE 1

Table 1: Analysis of the prognostic value of calreticulin in human malignancies Summary of statistical analyses is presented from clinical data in FIG. 4. Dichotomous HR and associated statistics reflect calreticulin expression cut-off around the median. Statistics are also presented for calreticulin expression when considered as a continuous variable with log-likelihood p values within a univariate Cox regression model. Therapy represents all possible therapies administered within each cohort.

| Disease (dataset) | FIG. | Data source | Patients (n) | Therapy | Dichotomous (median) | | | Continuous | | | Ref |
|---|---|---|---|---|---|---|---|---|---|---|---|
| | | | | | HR | 95% CI | P value | HR | Z-score | P value | |
| Neuroblastoma (1) | 4A | EBI Array Express: E-MTAB-179 | 478 | obs, surgery, L to HR-CX[+] | 1.70 | 1.23-2.35 | <0.005 | 2.25 | 4.07 | <0.0001 | 50 |
| Neuroblastoma (2) | 4B | EBI Array Express: E-TABM-38 | 251 | Obs, surgery, CTX, VCR, cisplatin, DOX | 1.78 | 1.10-2.87 | <0.05 | 4.78 | 3.11 | <0.005 | 51 |
| Superficial and invasive bladder cancer (1) | 4C | NCBI GEO: GSE135 07 | 165* | BCG, radical cystectomy/LN dissection, cisplatin-based chemo | 2.52 | 1.17-5.45 | <0.05 | 3.36 | 3.48 | <0.001 | 52 |
| Invasive bladder cancer (2) | 4D | NCBI GEO: GSE5287 | 30 | cisplatin-based chemo | 2.18 | 0.95-4.98 | 0.059 | 2.53 | 1.99 | <0.05 | 53 |
| Mantle cell Lymphoma (1) | 4E | NCBI GEO: GSE10793 | 71 | untreated | 2.57 | 1.35-4.89 | <0.005 | 3.02 | 3.19 | <0.005 | 54 |
| Mantle cell lymphoma (2) | 4F | LLMPP: Rosenwald_MCL | 92 | multi-agent chemo | 3.06 | 1.72-5.43 | <0.0001 | 1.72 | 4.12 | <0.0001 | 55 |

[+]first line therapy.
*91 patients in this dataset had missing clinical data.
Ref = reference, HR = hazard ratio, CI = confidence interval, obs = observation, L to HR-CX = low (<2 cycles) to high dose (≥6 cycles) cytotoxic therapy, BCG = bacillus calmette-guerin immunotherapy, CTX = cyclophosphamide, VCR = vincristine, DOX = doxorubicin, LN = lymph node. In this report, we identify calreticulin as a pro-phagocytic signal highly expressed on the surface of several human cancers, but minimally expressed on normal cell counterparts, and demonstrate that CRT expression is required for anti-CD47 antibody-mediated phagocytosis.

Anti-CD47 Antibody Preferentially Eliminates Tumor Cells Because of Differential Expression of Cell Surface Calreticulin.

We recently demonstrated that several cancers overexpress CD47 and that a blocking anti-CD47 monoclonal antibody can eliminate tumor cells in vitro and in vivo. These pre-clinical findings provide a strong rationale for the use of an anti-CD47 antibody in the treatment of human cancers. However, given the broad low level expression of CD47 on both hematopoietic and most other normal tissues, antibody toxicity could be a significant barrier to clinical translation.

To investigate this issue, we previously injected a blocking anti-mouse CD47 antibody into wild type mice at a dose that coated >98% of bone marrow cells but observed no overt toxicity, with the exception of isolated neutropenia. Moreover, a recent report demonstrated that inhibition of CD47 with either an antibody or morpholino could confer radioprotective effects to normal tissues. Here, we demonstrate that, despite low level CD47 expression, normal human cells from several tissues are not phagocytosed by human macrophages when coated with anti-CD47 antibody (FIG. 3B). We speculate that the selective phagocytosis of tumor cells is not simply dictated by CD47 expression level, but is also governed by the presence of the pro-phagocytic signal calreticulin, which is present on tumor cells but not on normal cells.

Several lines of evidence support this hypothesis. First, normal cells that express CD47 but not calreticulin are not phagocytosed with an anti-CD47 antibody despite being coated with the antibody (FIG. 3B). Second, tumor cells that express CD47 and calreticulin are phagocytosed when coated with anti-CD47 antibody (FIG. 3A,C). Third, phagocytosis of tumor cells with anti-CD47 antibody is completely abrogated when the calreticulin-LRP interaction is blocked (FIG. 3A,C). Fourth, adsorption of exogenous CRT onto the surface of NBM cells, which express minimal CRT (FIG. 1A), enabled increased phagocytosis compared to vehicle control or anti-CD47 antibody administration (FIG. 3E). Collectively, these findings demonstrate that calreticulin is necessary for anti-CD47 antibody-mediated phagocytosis, and that surface expression of this protein is primarily restricted to tumor cells.

This study indicates that the therapeutic window for anti-CD47 antibody therapy is not just a consequence of CD47 level on target cells, but that it also depends on the surface expression of pro-phagocytic calreticulin. On the basis of our findings, the overall contribution of pro (CRT)- and anti (CD47)-phagocytic signals determines whether normal or tumor cells are phagocytosed at steady state, or by anti-CD47 antibody therapy (FIG. 11). At steady state, tumor cells express calreticulin, but evade phagocytosis through overexpression of CD47, indicating the dominance of the "don't eat me" anti-phagocytic signal (FIG. 11A,B). Normal cells express low levels of CD47, and avoid phagocytosis because of a lack of CRT expression. In contrast, cells undergoing DNA damage or apoptosis express calreticulin on their cell surface, which is dominant over low CD47 expression and leads to phagocytosis. In the context of anti-CD47 antibody therapy, the anti-phagocytic signal (CD47) is blocked, unmasking the pro-phagocytic signal (CRT) on tumor cells, leading to phagocytosis (FIG. 11C,D). In contrast, blockade of CD47 on normal cells does not lead to phagocytosis since the pro-phagocytic "eat me" signal (CRT) is absent.

Although calreticulin appears to be primarily expressed on the surface of apoptotic or malignant cells, prior reports detected surface calreticulin on some human normal cells including activated peripheral blood T cells and circulating neutrophils. In addition, a blocking monoclonal anti-CD47 antibody enhances phagocytosis of apoptotic neutrophils. Interestingly, in our mouse toxicity studies, administration of a blocking anti-mouse CD47 antibody led to selective depletion of neutrophils, while other hematopoietic cells were unaffected. Similar to tumor cells, this selective neutropenic toxicity may be due to unmasking of calreticulin on neutrophils when the "don't eat me" signal (CD47) is blocked by anti-CD47 antibody. Although most normal cells do not express cell surface calreticulin, normal cells may upregulate calreticulin under certain conditions, including radiation and anthracycline-based chemotherapy as has been shown in some tumor types. Our findings provide a cautionary note that normal cells might upregulate calreticulin as a consequence of radiation and chemotherapy-based cancer therapy, and thus combination chemoradiation and anti-CD47 antibody therapy must be tested for potential increased toxicity to normal cells.

Calreticulin is the Dominant Pro-Phagocytic Signal on Several Human Cancers.

We demonstrate that several human cancers, including both hematopoietic and solid tumor malignancies, express the pro-phagocytic signal calreticulin. Known physiologic pro-phagocytic signals have previously been identified in several cancers including phosphatidylserine and annexin-1. However, most of these studies were not performed on primary human patient samples as in this study. Additionally, ligand expression appears to be mixed across tumor types with the functional role of these ligands in cancer not known. A complete survey of human tumors for cell surface calreticulin expression will be required to determine whether the regulation of the CD47-CRT phagocytic axis is a universal trait of cancers.

One key question is raised by these studies: Why do cancers express cell surface calreticulin, a pro-phagocytic signal? We have demonstrated that certain cancers evade the innate immune system by upregulating anti-phagocytic signals, specifically CD47. One might expect cancers to simultaneously downregulate pro-phagocytic signals to further increase their ability to evade macrophage phagocytosis. We propose two possible explanations. First, expression of cell surface calreticulin may be an unwanted consequence of cellular stress, whereby CD47 expression is upregulated to compensate and enable phagocytic evasion. In normal physiology, cell surface calreticulin is induced on cells undergoing DNA damage, marking these damaged cells for homeostatic phagocytosis. It is possible that a small fraction of these cells may selectively avoid phagocytic clearance due to higher levels or upregulation of CD47, which allows these damaged cells to survive and acquire additional mutations, eventually transforming into fully malignant cells. Several lines of evidence support this. First, CD47 and CRT expression are highly correlated in several human tumors (FIG. 2A). Second, the small percentage of live cells that are calreticulin positive in some normal human tissue types (bone marrow and bladder) express higher CD47 levels than their calreticulin negative counterparts (FIG. 7). Third, this increase in CD47 expression appears to protect against calreticulin-mediated phagocytosis as knockdown of CD47 to 50% of wild type levels enabled calreticulin-dependent phagocytosis (FIG. 2).

Expression of cell surface calreticulin may confer a pro-tumorigenic phenotype to cancer cells that is independent of phagocytosis. This hypothesis is supported by the finding that increased calreticulin expression in human tumors confers a worse clinical outcome across disparate tumor types, tumor stage, and tumor-specific therapies (FIG. 4). Cell surface calreticulin may allow more invasion and angiogenesis, as its ligand, LRP, is expressed on several vascular cell types. In two reports, overexpression of calreticulin or calreticulin fragments in tumor cell lines enhanced in vitro migration and invasion; however, other studies have reported alternative roles for calreticulin. In all of these studies the function of cell surface calreticulin was not distinguished from its intracellular roles. Other possible tumorigenic roles include cell adhesion and immune escape through reduction of MHC class I antigen presentation.

One key finding of our studies is the observation that increased levels of calreticulin corresponds to a more aggressive tumor phenotype and confers a worse clinical prognosis in several human malignancies. Given this finding and the restricted expression of cell surface calreticulin on tumor cells, calreticulin expression can be utilized in clinical diagnostics both in detection of cancer as well as monitoring of residual disease during therapy. Diagnostic modalities can include flow cytometry-based methods to detect cell surface calreticulin expression in the blood or bone marrow for hematologic malignancies or through imaging modalities utilizing a radio/fluorescent isotype coupled to cell surface calreticulin for the localization of human solid tumors. In addition to diagnostic utility, cell surface calreticulin may serve as a therapeutic target for human cancers. First, therapeutic agents with an agonist function that activates calreticulin-LRP signaling can enable phagocytosis of tumor cells. This specifically includes the generation of an agonist calreticulin antibody. Second, calreticulin antibodies can be coupled to a cytotoxic immunoconjugate to selectively target tumor cells given the tumor-restricted expression of calreticulin.

In summary, we have identified cell surface calreticulin as the dominant pro-phagocytic signal on several human cancers, which is absent on most normal cell counterparts and is required for anti-CD47 antibody-mediated phagocytosis. These findings support the development of an anti-CD47 antibody therapy for human malignancies, highlight the dynamic relationship between pro- and anti-phagocytic signals in human cancer, and provide a rationale for the diagnostic and therapeutic roles of targeting calreticulin.

Materials and Methods

Cell Lines and Human Samples.

MOLT4 and Daudi cell lines were obtained from the lab of Ronald Levy. 639V was obtained from the DSMZ. All other cell lines were obtained from the American Type Culture Association (ATCC). Normal human bone marrow mononuclear cells were purchased from AllCells Inc. Normal peripheral blood and human cancer samples were obtained from patients at the Stanford Medical Center with informed consent according to IRB-approved protocols: AML, ALL, and NHL human samples from Stanford IRB #76935, 6453, and 13500, bladder cancer samples from Stanford IRB #1512, glioblastoma samples from Stanford IRB #9363, and ovarian cancer samples from Stanford IRB #13939. Normal fetal bladder and brain cells were purchased from ScienCell Research Laboratories.

Flow Cytometry Analysis.

For analysis of normal peripheral blood cells, normal bone marrow cells, AML, CML, ALL, bladder cancer, ovarian cancer, and brain cancer, the following antibodies were used: CD34, CD38, CD90, CD45, CD31, CD3, CD4, CD7, CD11b, CD14, CD19, CD20, CD56, Glycophorin A (Invitrogen and BD Biosciences). Lineage negative (Lin–) was defined as CD3-CD19-CD20- for AML LSC and CD45-CD31- for GBM and bladder cancer CSC. Lin– was defined as CD3-CD4-CD7-CD8-CD11b-CD14-CD19-CD20-CD56-Glycophorin A- for NBM HSC, chronic phase CML GMP, CML CMP, and CML LSC. Analysis of CD47 expression was performed using an anti-human CD47 FITC antibody (clone B6H12.2, BD Biosciences). Analysis of human cell surface calreticulin expression was performed using mouse anti-human calreticulin conjugated to PE or FITC (clone FMC 75, Abcam). Human ERp57 expression was performed using a polyclonal rabbit anti-ERp57 antibody (Abcam) and then staining with a donkey anti-rabbit secondary antibody conjugated to PE (Ebioscience).

In Vitro Phagocytosis Assay.

Generation of human macrophages and in vitro phagocytosis assays were performed as previously described. Primary human samples or cell lines were incubated with 10 µg/ml IgG1 isotype control (Ebiosciences), 10 µg/ml anti-CD47 antibody (clone B6H12.2, ATCC), 4 µg/ml calreticulin blocking peptide (MBL International Corporation), 10 µg/ml RAP (Fitzgerald Industries International), or 125 µg/ml recombinant CRT human protein (Thermo Scientific). Per MBL, confirmation of blocking activity was performed by Western blot analysis, verified by incubation of an anti-CRT antibody with 5 times higher concentration of the peptide and performing a Western blot analysis to determine if the specific band had been diminished. Cells were then analyzed by fluorescence microscopy to determine the phagocytic index (number of cells ingested per 100 macrophages).

shRNA Knockdown of Raji Cells.

shRNA constructs targeting knockdown of human CD47 or a GAPD control packaged in the SMARTvector 2.0 lentiviral vector containing a turbo GFP reporter were purchased from Dharmacon, Inc. (Lafayette, Colo.). Viral titers for each shRNA construct were greater than 10>8 TU/ml. Raji cells were transduced with these lentiviral constructs, analyzed and sorted for GFP expression, expanded, and sorted again for GFP expression for stable propagation of lentivirally-transduced cells. Knockdown of CD47 protein levels was assessed by flow cytometry with anti-CD47 antibody (B6H12.2) with fold knockdown calculated by reduction in MFI normalized over isotype control.

Xenotransplantation of Primary Human Cancer Cells into Mice.

For engraftment of human AML cells, AML LSC (CD34+CD38-CD90-Lin–) were sorted by fluorescence-activated cell sorting (FACS) and transplanted into the facial vein of newborn NOD.Cg-Prkdc$_{scid}$Il2rg$_{tm1Wjl}$/SzJ (NSG) mice, sublethally-irradiated with 200 rads. Leukemic engraftment was analyzed 8 weeks later in the bone marrow of transplanted mice. For engraftment of human bladder cancer, bulk bladder cancer cells were resuspended in 25% matrigel (BD Biosciences) and transplanted subcutaneously into the flanks of adult NSG mice. Tumor volume was serially monitored post-transplantation by analyzing weights of excised tumors.

Analysis of Prognostic Value of Calreticulin in Human Malignancies.

Gene expression and clinical data were analyzed for six previously described cohorts of neuroblastoma, superficial and invasive urothelial carcinoma of the bladder, and mantle cell lymphoma (see table 1 for dataset descriptions). Patients were stratified into high and low calreticulin expression groups based on the median expression level within each cohort and analyzed for event-free, disease-specific, or overall survival by Kaplan-Meier analysis. Subsequent dichotomous hazard ratios, 95% confidence intervals, and log-rank p-values were analyzed reflecting estimates within Kaplan-Meier analyses (table 1). Additionally, analyses were performed based on continuous expression of calreticulin and clinical outcome as measured by log-likelihood p-values within a univariate Cox regression model (table 1). Affymetrix microarray data were processed starting with CEL files, with Entrez Gene probeset summarization using CustomCDF version 12 (49), and normalization using MAS 5.0 linear scaling method. Overlapping samples from related studies (FIGS. 4A,B and 4E,F), have not been removed.

What is claimed is:

1. A method of administering an anti-CD47 therapy to an individual with cancer during a therapeutic window, the method comprising: detecting calreticulin on non-cancerous normal cells in a sample obtained from the individual, by binding the sample to an antibody specific for calreticulin; and administering an effective dose of a soluble SIRPa protein during a therapeutic window when non-cancerous cells do not express calreticulin.

2. The method of claim 1, wherein said normal cells are hematopoietic stem and/or progenitor cells.

3. The method of claim 1 wherein said normal cells are blood cells and/or platelets.

4. The method of claim 1 wherein said normal cells are tissue stem and/or progenitor cells detected in tissue biopsies, including intestinal crypt cells, or lung cells.

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Synthetic amino acid sequence

<400> SEQUENCE: 1

Lys Leu Gly Phe Phe Lys Arg
1               5

<210> SEQ ID NO 2
<211> LENGTH: 49
<212> TYPE: PRT
<213> ORGANISM: Artificial Sequence
<220> FEATURE:
<223> OTHER INFORMATION: Synthetic amino acid sequence

<400> SEQUENCE: 2

Lys Glu Glu Glu Glu Asp Lys Lys Arg Lys Glu Glu Glu Ala Glu
1               5                   10                  15

Asp Lys Glu Asp Asp Glu Asp Lys Asp Glu Asp Glu Glu Asp Glu
                20                  25                  30

Asp Lys Glu Glu Asp Glu Glu Glu Asp Val Pro Gln Ala Lys Asp Glu
        35                  40                  45

Leu
```